US 11,912,744 B2

(12) United States Patent
Herzberg et al.

(10) Patent No.: US 11,912,744 B2
(45) Date of Patent: Feb. 27, 2024

(54) NON-TRANSGENE TRANSFECTION FOR THERAPEUTIC PURPOSES

(71) Applicant: Antibiotic Alternatives LLC, Minneapolis, MN (US)

(72) Inventors: Mark C. Herzberg, Minneapolis, MN (US); Karen Farnie Ross, St. Paul, MN (US); Brent S. Sorenson, Minneapolis, MN (US)

(73) Assignee: Antibiotic Alternatives LLC, Minneapolis, MN (US)

( * ) Notice: Subject to any disclaimer, the term of this patent is extended or adjusted under 35 U.S.C. 154(b) by 61 days.

(21) Appl. No.: 16/842,489

(22) Filed: Apr. 7, 2020

(65) Prior Publication Data
US 2020/0231640 A1 Jul. 23, 2020

Related U.S. Application Data

(62) Division of application No. 14/760,077, filed as application No. PCT/US2014/011041 on Jan. 10, 2014, now abandoned.

(60) Provisional application No. 61/751,504, filed on Jan. 11, 2013.

(51) Int. Cl.
| | |
|---|---|
| *A61K 48/00* | (2006.01) |
| *C12N 15/87* | (2006.01) |
| *C12N 15/52* | (2006.01) |
| *A61K 31/7105* | (2006.01) |
| *C12N 15/12* | (2006.01) |
| *C07K 14/47* | (2006.01) |

(52) U.S. Cl.
CPC .............. *C07K 14/47* (2013.01); *A61K 48/00* (2013.01); *A61K 48/005* (2013.01); *C12N 15/87* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 7,927,873 B2 | 4/2011 | Reineke et al. | |
| 8,501,478 B2 | 8/2013 | Reineke et al. | |
| 8,916,163 B1* | 12/2014 | Skaar .................. | A61K 38/1738 424/184.1 |
| 2003/0003482 A1 | 1/2003 | Halle et al. | |
| 2006/0034820 A1* | 2/2006 | Lim ....................... | A61K 38/47 424/94.61 |
| 2006/0084620 A1 | 4/2006 | McCray et al. | |
| 2006/0223121 A1 | 10/2006 | Roecklin et al. | |
| 2007/0123455 A1* | 5/2007 | Palefsky ................. | A61P 29/00 514/1.7 |
| 2009/0305963 A1 | 12/2009 | Sukhatme et al. | |
| 2012/0251618 A1* | 10/2012 | Schrum ................ | C07K 14/535 424/450 |
| 2013/0336950 A1* | 12/2013 | Wehkamp ............... | A61P 31/04 424/94.4 |
| 2014/0128313 A1* | 5/2014 | Bishop ..................... | C07K 7/08 514/2.4 |

FOREIGN PATENT DOCUMENTS

| | | |
|---|---|---|
| WO | 01/23002 A1 | 4/2001 |
| WO | 2004106519 | 12/2004 |

OTHER PUBLICATIONS

Miller and Cho, Immunity against *Staphylococcus aureus* cutaneous infections, Nature, 2011, p. 505-518.*
Hans and Hans, Epithelial Antimicrobial Peptides: Guardian of the Oral Cavity, International Journal of Peptides, 2014, pp. 1-13.*
Ferrari et al, Mucus altering agents as adjuncts for nonviral gene transfer to airway epithelium, Gene Therapy (2001) 8, 1380-1386.*
Toyanaga et al, Lipocalin 2 prevents intestinal inflammation by enhancing phagocytic bacterial clearance in macrophages, Scientific Reports, 2016, pp. 1-13.*
Zheng et al, Topical delivery of siRNA-based spherical nucleic acid nanoparticle conjugates for gene regulation, PNAS, 2012, pp. 11975-11980.*
Preat and Dujardin, Topical delivery of nucleic acids in the skin, STP PharaSciences, 2001, pp. 1-12.*
Granstein et al, Induction of Anti-Tumor Immunity with Epidermal Cells Pulsed with Tumor-Derived RNA or Intradermal Administration of RNA, J Invest Dermatol 114:, 2000, pp. 632-636.*
Hu et al, Embryonic Skin Development and Repair, Organogenesis • Feb. 2018, p. 46-63.*
Solaro et al, Targeted Delivery of Protein Drugs by Nanocarriers, Materials 2010, 3, 1928-1980.*
Su et al, In vitro and in vivo mRNA delivery using lipid-enveloped pH responsive polymer nanoparticles, Mol Pharm. 2011, 8(3): 774-787.*
American Type Culture Collection—KB (ATCC CCL-17) URL: https://www.atcc.org/Products/All/CCL-17.aspx#characteristics.
Jiang, L. et al. "Cell line cross-contamination: KB is not an oral squamous cell carcinoma cell line," European Journal of Oral Sciences, 2009, 117:90-91.
Nisapakultorn, K. et al., "Calprotectin expression in vitro by oral epithelial cells confers resistance to infection by Prophyromonas gingivalis," Infection and Immunity, Jul. 2001, vol. 69, No. 7, pp. 4242-4247.

(Continued)

*Primary Examiner* — Maria Marvich
(74) *Attorney, Agent, or Firm* — QUARLES & BRADY LLP

(57) ABSTRACT

This disclosure describes compositions and methods involved in tumor suppression and inhibiting infection of cells by pathogens. Generally, the compositions include an mRNA cargo that can provide a therapeutic benefit after being introduced into an epithelial cell. In some cases, the mRNA can encode a polypeptide. In some cases, the polypeptide can suppress epithelial cell proliferation. In other embodiments, the polypeptide can be involved in innate immunity. In various embodiments, the polypeptide can include cathelicin antimicrobial protein (CAMP), calprotectin, S100A8, S100A9, a β-defensin, S100A7, secretory leukocyte inhibitor, lipocalin 2, or lysozyme. In some embodiments, the mRNA can include a stabilizing moiety such as, for example, a 5' cap or a 3' extension.

25 Claims, 16 Drawing Sheets

Specification includes a Sequence Listing.

(56) References Cited

OTHER PUBLICATIONS

Flo et al: "Lipocalin 2 mediates an innate immune response to bacterial infection by sequestrating iron", Nature, vol. 432, No. 7019, Dec. 16, 2004, pp. 917-921.
Fernie-King B A et al: "Streptococcal Inhibitor of Complement Inhibits Two Additional Components of the Mucosal Innate Immune System: Secretory Leukocyte Proteinase Inhibitor and Lysozyme", Infection and Immunity, American Society for Microbiology, US, vol. 70, No. 9, Sep. 1, 2002, pp. 4908-4916.
Kisich et al: "Antimycobacterial Agent Based on mRNA Encoding Human Defensin 2 Enables Primary Macrophages To Restrict Growth of *Mycobacterium tuberculosis*", Infection and Immunity, vol. 69, No. 4, Apr. 1, 2001, pp. 2692-2699.
Kormann et al: "Expression of therapeutic proteins after delivery of chemically modified mRNA in mice", Nature Biotechnology, vol. 29, No. 2, Feb. 1, 2011, pp. 154-157.
Nisapakultorn et al: "Calprotectin Expression Inhibits Bacterial Binding to Mucosal Epithelial Cells" Infection and Immunity, vol. 69, No. 6, Jun. 1, 2001 pp. 3692-3696.
Glaser et al: 11 Antimicrobial psoriasin (S100A7) protects human skin from *Escherichia coli* infection, Nature Immunology, Nature Publishing Group, GB, vol. 6, No. 1, Jan. 1, 2005, pp. 57-64.
Sorenson et al: "IL-1 receptor regulates S100A8/A9-dependent keratinocyte resistance to bacterial invasion", Mucosal Immunology, vol. 5, No. 1, Jan. 1, 2012, pp. 66-75.
Tavernier et al: "mRNA as gene therapeutic: How to control protein expression", Journal of Controlled Release, vol. 150, No. 3, Mar. 1, 2011 (Mar. 1, 2011), pp. 238-247.
Wiesner et al: "Antimicrobial peptides: The ancient arm of the human immune system", Virulence, Sep. 1, 2010, pp. 440-464.
Yamamoto et al: "Current prospects for mRNA gene delivery", European Journal of Pharmaceutics and Biopharmaceutics, Elsevier Science Publishers B.V., Amsterdam, NL, vol. 71, No. 3, Mar. 2009 (Mar. 3, 2009), pp. 484-489.

Zou et al: Paper: High-efficiency Delivery of Antimicrobial mRNAs into Human Mucosal Epithelial Cells (AADR Annual Meeting (Mar. 21-24, 2012).
Zou et al: Augmentation of Epithelial Resistance to Invading Bacteria by Using mRNA Transfections, Infection and Immunity, vol. 81, No. 11, Aug. 12, 2013, pp. 3975-3983.
Khammanivong, Ali, et al. "S100A8/A9 (calprotectin) negatively regulates G2/M cell cycle progression and growth of squamous cell carcinoma." PLoS One 8.7 (Jul. 2013): e69395.
Tavernier, Geertrui, et al. "mRNA as gene therapeutic: how to control protein expression." Journal of Controlled Release 150.3 (Oct. 2011): 238-247.
Voss, Andreas, et al. "Expression of S100A8/A9 in HaCaT keratinocytes alters the rate of cell proliferation and differentiation." FEBS letters 585.2 (Dec. 2011): 440-446.
Bettinger, T et al. Peptide-Mediated RNA Delivery: A Novel Approach For Enhanced Transfection Of Primary And Post-Mitotic Cells. Nucleic Acids Research. Sep. 15, 2001, vol. 29; pp. 3882-3891.
Khammanivong, A. Regulatory Roles Of Calprotectin In Head And Neck Squamous Cell Carcinogenisis. A Dissertation Submitted to the Faculty of the Graduate School of the University of Minnesota. Jul. 2011.
Hiroshima, Y. et al. Shosaikoto Increases Calprotectin Expression In Human Oral Epithelial Cells. Journal or Periodontal Research. Jul. 8, 2009, vol. 45; pp. 79-86.
Bando, M et al. Interleukin-1-alpha Regulates Antimicrobial Peptide Expression In Human Keratinocytes. Immunology and Cell Biology. Jun. 5, 2007, vol. 85; pp. 532-537.
Warren, et al. Highly efficient Repgorgraming to Pluripotency and Directed Differentiationof Human Cells with Synthetic Modified mRNA. Cell Stem Cell. 2010. 7(5): 618-630.
Grudzien-Nogalska et al., Synthesis of anti-reverse cap analogs (ARCAs) and their applications in mRNA translation and stability. Methods Enzymol. 2007;431:203-27.

* cited by examiner

NON-TRANSGENE TRANSFECTION FOR THERAPEUTIC PURPOSES

CROSS-REFERENCE TO RELATED APPLICATION

This application is a divisional of U.S. application Ser. No. 14/760,077, filed Jul. 9, 2015, which is a 371 U.S. National Phase Entry of International Patent Application No. PCT/US2014/011041, filed Jan. 10, 2014, which claims priority to U.S. Provisional Patent Application Ser. No. 61/751,504, filed Jan. 11, 2013, each of which is incorporated herein by reference in their entireties.

GOVERNMENT FUNDING

This invention was made with government support under 1R01DE021206 awarded by the NIH/NIDCR. The Government has certain rights in the invention.

REFERENCE TO A SEQUENCE LISTING SUBMITTED VIA EFS-WEB

The content of the ASCII text file of the sequence listing named "154942_00007_seqlist txt.txt" which is 3.87 kb in size was created on Dec. 29, 2016 and electronically submitted via EFS-Web herewith the application is incorporated herein by reference in its entirety.

SUMMARY

This disclosure describes, in one aspect, a method of suppressing cell proliferation. Generally the method includes introducing into an epithelial cell an mRNA encoding a polypeptide involved in suppressing cell proliferation and permitting the cell to express the polypeptide in an amount effective to decrease the likelihood that the cell proliferates in an anchorage-independent environment. In some embodiments, the polypeptide can include calprotectin (S100A8 complexed with S100A9; S100A8/A9), S100A8, or S100A9.

In another aspect, this disclosure describes a method of inhibiting infection of a cell. Generally, the method includes introducing into a cell an mRNA encoding a polypeptide involved in innate immunity and permitting the cell to express the polypeptide in an amount effective to decrease the likelihood that the cell is infected by a pathogen. In some embodiments, the polypeptide can include cathelicin antimicrobial protein (CAMP), calprotectin, S100A8, S100A9, a β-defensin, S100A7, secretory leukocyte inhibitor, lipocalin 2, or lysozyme.

In some embodiments of either aspect summarized above, the mRNA can include a stabilizing moiety such as, for example, a 5' cap or a 3' extension. In some embodiments, the cell can be a mucosal epithelial cell.

In another aspect, this disclosure describes a composition that generally includes an mRNA that encodes a polypeptide and an in vivo delivery vehicle.

In some embodiments, the polypeptide can suppress epithelial cell proliferation. In some of these embodiments, the polypeptide can include calprotectin, S100A8, or S100A9. In other embodiments, the polypeptide can be involved in innate immunity. In some of these embodiments, the polypeptide can include cathelicin antimicrobial protein (CAMP), calprotectin, S100A8, S100A9, a β-defensin, S100A7, secretory leukocyte inhibitor, lipocalin 2, or lysozyme. In some embodiments, the mRNA can include a stabilizing moiety such as, for example, a 5' cap or a 3' extension.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
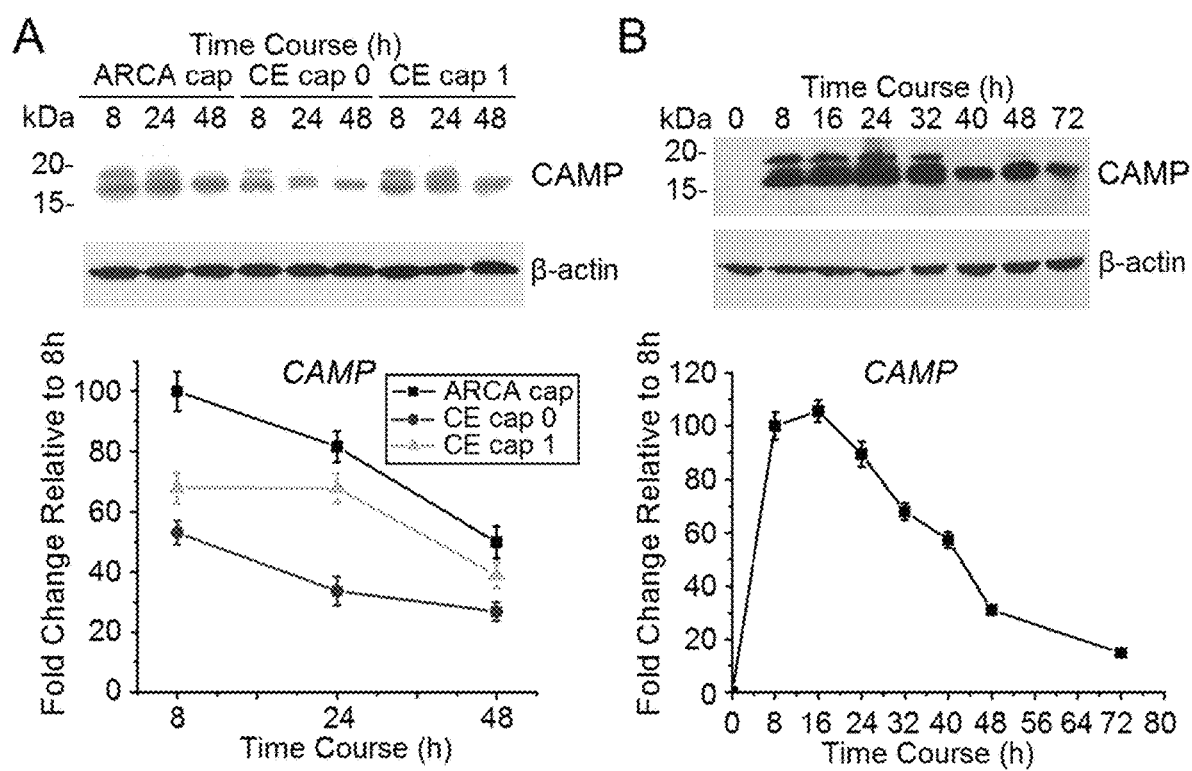
FIG. 1. CAMP protein expression by KB cells after transfection with ARCA-capped CAMP mRNA or CE capped CAMP mRNA. (A) CAMP protein expression after KB cells were transfected with ARCA, CE cap0, or cap1-capped CAMP mRNA. Upper, representative Western blot. Lower, quantitative interpretation, with ARCA cap expression at eight hours set to 100. After analysis using Quantity One analysis as described in the Materials and Methods, protein expression after transfection with the several capping methods was presented relative to 100. (B) CAMP protein expression over time after transfection with ARCA-capped CAMP. As in panel (A), CAMP protein expression after ARCA-capped CAMP mRNA transfection was detected using Western blot (upper panel) and presented in the lower panel relative to the level at eight hours, which is set to 100. In panels (A) and (B), the error bars show the means±SD of three to six independent experiments.

This disclosure relates to compositions and methods that involve introducing an mRNA into a cell so that the cell expresses one or more polypeptides that can decrease the likelihood and/or extent to which the cell functions abnormally and/or is susceptible to infection by a pathogen. Thus, the methods and compositions can provide therapy against conditions that result from infection including, for example, infectious diseases and certain neoplasms. Once introduced into a cell, the polypeptide is expressed only as long as the mRNA can be translated in the target cells—i.e., expression is transient, not permanent. If the cells form a target tissue that is accessible, the mRNA can be re-introduced repeatedly for sustained therapeutic benefit.

Mucosal epithelia provide the first line of defense against the invasion of microbes. Oral and other mucosal epithelial cells confer protection against invading bacteria through a cell autonomous mechanism using two effector antimicrobial peptides (AMPs), calprotectin (S100A8/S100A9 heterodimer) in the cytosol and cathelicidin antimicrobial protein (CAMP) in endosomes. To learn whether innate immunity might be benignly augmented, we transiently transfected epithelial cells with optimized mRNA constructs containing either CAMP, S100A8 and S100A9 open reading frames, A8-IRES-A9 (fusion), or A8-nIRES-A9 (fusion, native IRES). To maintain stability of the mRNA, CAMP mRNA capped with anti-reverse cap analogue (ARCA) was more effective than the capping enzyme (CE) cap 0 or CE 1. CAMP, S100A8, and S100A9 protein levels generally peaked at 16 hours after mRNA transfection. In contrast, cotransfection with S100A8/S100A9 resulted in maximal protein expression at 24 hours. After transfection with tandem mRNAs (A8-IRES-A9 and A8-nIRES-A9), S100A8 protein levels were maximal at 16 hours, whereas S100A9 peaked at 32 hours to 40 hours. Following transfection with the respective mRNAs, CAMP and calprotectin each significantly increased resistance of epithelial cells to invasion by *Listeria* and *Salmonella* for up to 48 hours; co-transfection of S100A8/S100A9 was more effective than the tandem constructs. The transfections reduced cell viability after 48 hours by 20%, with only 2% attributable to apoptosis. Taken together, these results suggest that epithelial cell resistance to invasive pathogens can be augmented by transient transfection of antimicrobial mRNAs into epithelial cells.

Human CAMP is a member of a large family of cationic antimicrobial peptides expressed in many species that have broad-spectrum activity against bacteria, fungi, and enveloped viruses and also show immunomodulatory effects (Zanetti, 2004. *J. Leukoc. Biol.* 75: 39-48; Bucki et al., 2010. *Arch. Immunol. Ther. Exp. (Warsz).* 58: 15-25; Strandberg et al., 2012. *Infect. Immun.* 80: 3930-3938; Burton et al., 2009. *Nat. Prod. Rep.* 26: 1572-1584). Following excision of the signal peptide, human CAP-18 precursor encoded by CAMP is stored in neutrophil granules and epithelial cells until activated through cleavage by proteinase 3, a serine protease (Sorensen et al., 2001. *Blood* 2001, 97: 3951-3959). The 37-residue active peptide (LL-37) mediates a wide range of biological responses such as, for example, direct killing of microorganisms, chemotaxis and chemokine induction, regulation of inflammatory responses, and adjuvant, angiogenic, and wound healing effects (Nijnik et al., 2009. *Curr. Opin. Hematol.* 16: 41-47). LL-37 appears to be directly antimicrobial in the phagolysosomes of neutrophils and macrophages and at sites of acute inflammation (Nijnik et al., 2009. *Curr. Opin. Hematol.* 16: 41-47), showing broad spectrum antimicrobial activity against *Listeria monocytogenes* (Turner et al., 1998. *Antimicrob. Agents Chemother.* 42: 2206-2214), *Salmonella typhimurium* (Larrick et al., 1995. *Immunotechnology* 1: 65-72), and *Streptococcus* group A, B and C (Dorschner et al., 2001. *J. Invest. Dermatol.* 117: 91-97). CAMP expression can be induced by 1,25-dihydroxyvitamin D3 (Wang et al., 2004. *J. Immunol.* 173: 2909-2912), pathogens (Midorikawa et al., 2003. *Infect. Immun.* 71: 3730-3739; Nijnik et al., 2009. *Curr. Opin. Hematol.* 16: 41-47) or lipopolysaccharide (LPS) (Nell et al., 2004. *FEMS Immunol. Med. Microbiol.* 42: 225-231). Decreased CAMP/LL-37 production accompanies increased invasion and colonization of pathogens in epithelial cells in diseases such as, for example, morbus Kostmann and Papillon-Lefevre syndrome (Carlsson et al., 2006. *J. Periodontol.* 77: 744-751; de Haar et al., 2006. *Infect. Immun.* 74: 5284-5291), Crohn's disease (Schauber et al., 2006. *Mol. Nutr. Food Res.* 50: 1006-1012) and atopic dermatitis (Ong et al., 2002. *N. Engl. J. Med.* 347: 1151-1160).

Calprotectin is a heterodimeric complex of calcium-binding proteins S100A8 (MRP8 or calgranulin A, 10.8 kDa) and S100A9 (MRP14 or calgranulin B, 13.2 kDa) (Champaiboon et al., 2009. *J. Biol. Chem.* 284:7078-90). S100A8 and S100A9 are members of the S100 family of proteins. Family members contain two EF-hand calcium-binding motifs and the proteins are involved in cell growth, cell differentiation, cell cycle progression, cell survival, protein phosphorylation, transcription, cancer development and inflammatory diseases (Donato, 2001. *Int. J. Biochem. Cell Biol.* 33: 637-668; Santamaria-Kisiel et al., 2006. *Biochem. J.* 396: 201-14; Khammanivong et al., 2013. *PLoS One* 8: e69395). The calcium-binding motifs appear to be involved in epithelial cell resistance to bacterial invasion (Champaiboon et al., 2009. *J. Biol. Chem.* 284:7078-90). Calprotectin shows broad spectrum antimicrobial activity against mucosal and epidermal *Candida albicans* and bacteria including *Capnocytophaga sputigena, Escherichia coli, Staphylococcus epidermis, Listeria monocytogenes, Salmonella typhimurium*, and *Porphyromonas gingivalis* (Champaiboon et al., 2009. *J. Biol. Chem.* 284:7078-90; Miyasaki et al., 1993. *J. Dent. Res.* 72: 517-523; Sohnle et al., 1991. *J. Infect. Dis.* 163: 187-192; Steinbakk et al., 1990. *Lancet* 336: 763-765; Nisapakultorn et al., 2001. *Infect. Immun.* 69: 4242-4247). To facilitate intraepithelial survival after successful invasion, *Listeria* mobilizes calprotectin to co-localize with cytoplasmic microtubules, appearing to subvert anti-*Listeria* activity and autonomous cellular immunity (Zaia et al., 2009. *Mucosal Immunol.* 2: 43-53).

Mucosal epithelial cells, therefore, can protect against and suppress invasive pathogens mainly using two antimicrobial effector systems, CAMP/LL-37 largely in endosomes (Chamilos et al., 2012. *Blood* 120: 3699-3707) and calprotectin (S100A8/S100A9) in the cytosol (Champaiboon et al., 2009. *J. Biol. Chem.* 284:7078-90). We describe herein a manner in which intra-epithelial cell resistance against invasive microbial pathogens can be increased by transient delivery of specific antimicrobial effector mRNAs (e.g., CAMP, S100A8/S100A9). mRNA transfections for therapeutic purposes can replace or augment expression of proteins through systemic or ex vivo administration (Tavernier et al., 2011. *J. Control. Release.* 150: 238-47). This approach avoids transfection with DNA and the attendant challenges including, for example, imprecise, mutagenic insertion into the host cells. With a view towards augmenting mucosal innate immunity, we report the delivery of CAMP and S100A8/S100A9 mRNAs into human epithelial cells and the functional antibacterial effects of those transfections.

Optimizing mRNA Stability

Capping at the 5' end of mRNA enhances the stability of the expressed message. An ARCA can cap at an efficacy up to 80% and the capping enzyme (CE) can increase capping efficiency to 100% (Zhao et al., 2010. *Cancer Res.* 70: 9053-9061). To optimize the capping strategy, we compared mMESSAGE mMACHINE® T7 Ultra (Life Technologies Corp., Carlsbad, CA), which generates ARCA-capped mRNA, with the mScript™ RNA System (Cell Script Inc., Madison, WI), which uses capping enzyme (CE), and 2'-O-Methyltransferase capping enzyme to generate a cap 0 or cap 1. CAMP mRNAs were synthesized using the different capping systems, delivered into KB cells and protein expression was detected by western blot analysis. At eight hours, 24 hours, and 48 hours after transfection with ARCA-capped mRNAs, KB cells expressed more CAMP protein than after transfection with CE cap 1, which was higher than CE cap 0 (FIG. 1A). CAMP protein levels peaked at about 16 hours and decreased by about 50% at 40 hours to 48 hours after ARCA capped mRNA delivery (FIG. 1B). ARCA capping was then used for all experiments. We also compared mRNA stability when expressed with 3' extensions of 64A and 150A. There was little difference (data not shown) and we used 150A for all subsequent experiments.

Stability of mRNAs Capped with Anti-Reverse Cap Analogue (ARCA)

Figure 5:
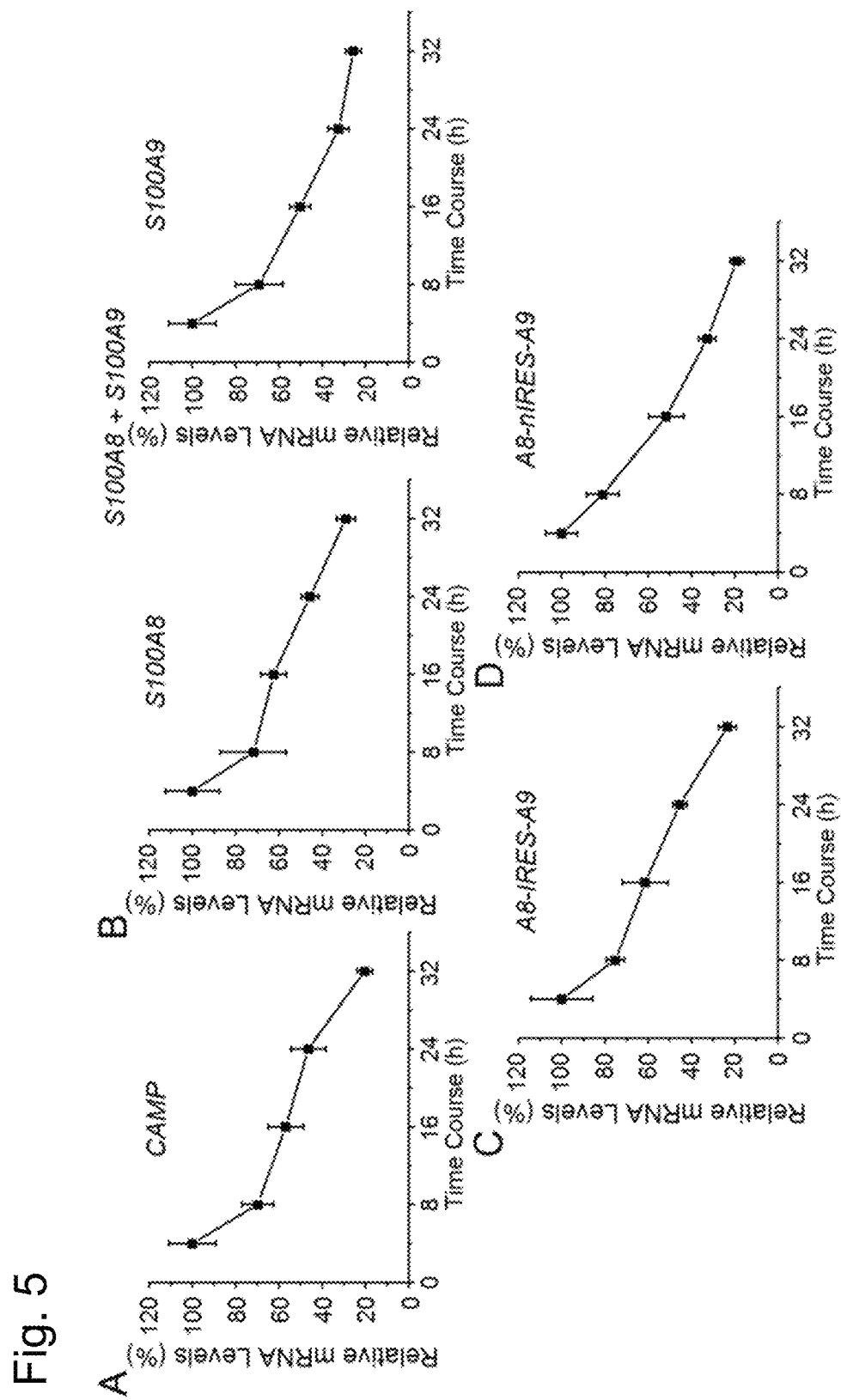
FIG. 5. Antimicrobial mRNAs persist for up to 32 hours in KB cells. RNA was isolated using Trizol reagent (Life Technologies Corp., Carlsbad, CA) and RNeasy plus Mini-kits (Qiagen, Valencia, CA). Total RNA was reverse transcribed with Superscript III (Life Technologies Corp., Carlsbad, CA). Quantitative Real-time Polymerase Chain Reaction (qRT-PCR) was performed using PrimeTime pre-designed qRT-PCR assays (Hs.PT.42.1073747 for human CAMP, Hs.PT.42.3682141 for human S100A8, Hs.PT.42.3080635 for human S100A9, Hs.PT.45.227970.g for human ACTB; Integrated DNA Technologies, Coralville, Iowa). The expression levels of CAMP, S100A8, S100A9 A8-IRES-A9 and A8-nIRES-A9 mRNA were normalized to ACTB (β-actin) mRNA. (A) CAMP mRNA transfection. (B) S100A8/S100A9 mRNA (mol/mol=1:1) cotransfection. (C) A8-IRES-A9 mRNA transfection. (D) A8-nIRES-A9 mRNA transfection. A8-IRES-A9 and A8-nIRES-A9 mRNAs were detected by S100A9 primers. mRNA abundance at four hours after mRNA transfection was assigned the arbitrary value of 100%. Bars show the means±SD of three to six independent experiments.

KB cells natively express mRNA for CAMP, S100A8, and S100A9 below the level of detection (data not shown). Therefore, endogenous S100A8, S100A9, and CAMP mRNAs expressed in KB cells will contribute little to subsequent levels after transfection with ARCA-capped mRNAs. To synthesize a fusion mRNA that contains both S100A8 and S100A9, an S100A8 ORF containing a Kozak sequence was cloned into pIRES MCS A and S100A9 was cloned into MCS B. To eliminate the attenuation of downstream translation with pIRES, native IRES (nIRES) was constructed and inserted between S100A8 and S100A9 ORFs. Sequences containing all necessary elements were cloned into pGEM4Z.2bgUTR.150A, and then A8-IRES-A9 and A8-nIRES-A9 mRNAs were synthesized. Transfection of in vitro transcribed ARCA-capped CAMP, S100A8, S100A9, A8-IRES-A9, and A8-nIRES-A9 mRNAs were analyzed using qRT-PCR (FIG. 5). At four hours after each mRNA transfection, the specific intracellular mRNAs were at the highest level measured. At 16 hours to 20 hours following transfection, the CAMP mRNA level was approximately half that at four hours, indicating that the half-life in KB cells was between 12 hours and 16 hours (FIG. 5A). In contrast, co-transfection of S100A8 mRNAs resulted in mRNA half-lives of 12 hours to 16 hours, while co-transfection of S100A9 mRNAs resulted in mRNA half-lives of eight hours to 12 hours (FIG. 5B). When the tandem mRNAs were transfected, the half-life of A8-IRES-A9 was 12 hours to 16 hours whereas the half-life of A8-nIRES-A9 mRNA was eight hours to 12 hours (FIG. 6C, 6D). The half-lives of these mRNAs were eight hours to 16 hours in KB cells.

Co-Transfection of S100A8 and S100A9 Increases Stability of Each Protein

Figure 2:
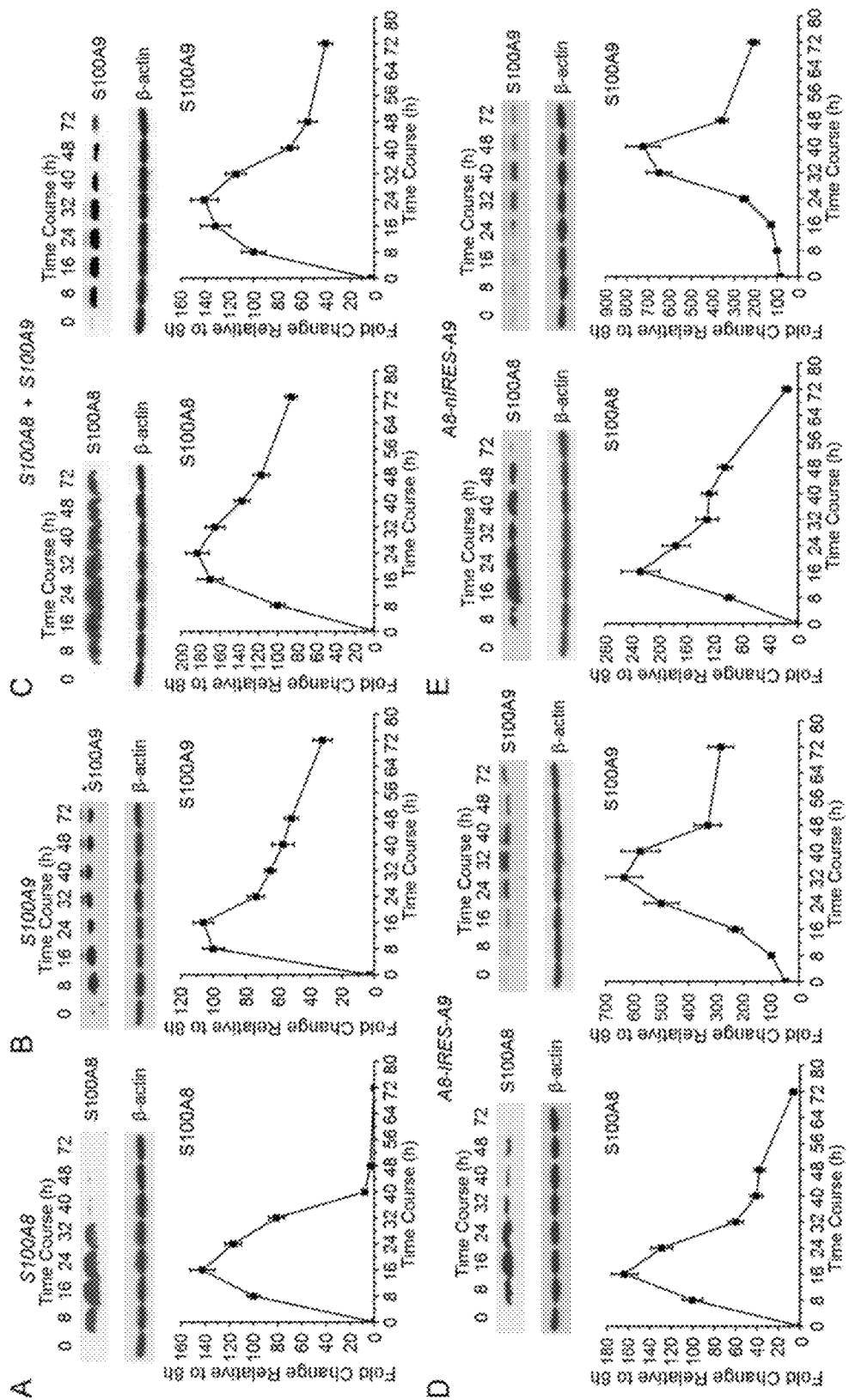
FIG. 2. S100A8 and S100A9 protein expression by KB cells after transfection with ARCA-capped S100A8, S100A9, A8-IRES-A9, and A8-nIRES-A9 mRNA. (A) S100A8 protein expression after KB cells were transfected with S100A8 mRNA as detected using Western blot (representative image shown) and quantitated as in FIG. 1. Identical experiments were performed to determine the time course of expression of (B) S100A9 protein; (C) S100A8 and S100A9 protein after KB cells were cotransfected with S100A8/S100A9 mRNA; (D) S100A8 and S100A9 protein after KB cells were transfected with A8-IRES-A9 mRNA; and (E) S100A8 and S100A9 protein after KB cells were transfected with A8-nIRES-A9 mRNA. Protein expression at 8 h after mRNA transfection is set as 100. Error bars show the means±SD of three to six independent experiments.

After delivery into KB cells, ARCA-capped mRNAs for S100A8 (FIG. 2A), S100A9 (FIG. 2B), and calprotectin (1:1 mol/mol S100A8+S100A9) (FIG. 2C) were compared for protein expression. Expression of S100A8 protein alone was maximal at 16 hours and decreased by about half at about 28 hours (FIG. 2A), whereas S100A9 protein maximized at 16 hours and decreased to half at about 40 hours to 48 hours (FIG. 2B). In contrast, co-transfection of S100A8 and S100A9 mRNAs (half the amount of each compared to transfections with either S100A8 or S100A9) appeared to increase the stability of each peptide. Unlike S100A8 for example (FIG. 2A), each protein was expressed throughout the time course (FIG. 2C, 2D). For S100A8, protein maximized at 24 hours and decreased by half at about 72 hours (FIG. 2C). When co-transfected with S100A8, S100A9 protein also maximized at 24 hours and decreased to half at about 48 hours to 72 hours (FIG. 2C). Co-transfection of S100A8 and S100A9 mRNA led to increased stability of each peptide suggesting that calprotectin heterodimer formation is preferred.

S100A8/S100A9 Protein Expression Using Tandem Constructs

After A8-IRES-A9 mRNA transfection, S100A8 protein expression was maximal at 16 hours and decreased to half at 24 hours to 32 hours (FIG. 2D), whereas S100A9 protein maximized at 32 hours and decreased to half at about 48 hours to 72 hours (FIG. 2D). For A8-nIRES-A9 mRNA transfection, expression of S100A8 protein was maximal at 16 hours and decreased to half at 24 hours to 32 hours (FIG. 2E), whereas S100A9 protein was maximal at 40 hours and decreased to half at about 40 hours to 48 hours (FIG. 2E). As when S100A8 was co-expressed with S100A9 (FIG. 2C), use of the tandem mRNA constructs generally appeared to stabilize the protein subunits when compared with only S100A8 mRNA transfection (FIG. 2A).

Intracellular Presentation of CAMP and Calprotectin

Figure 6:
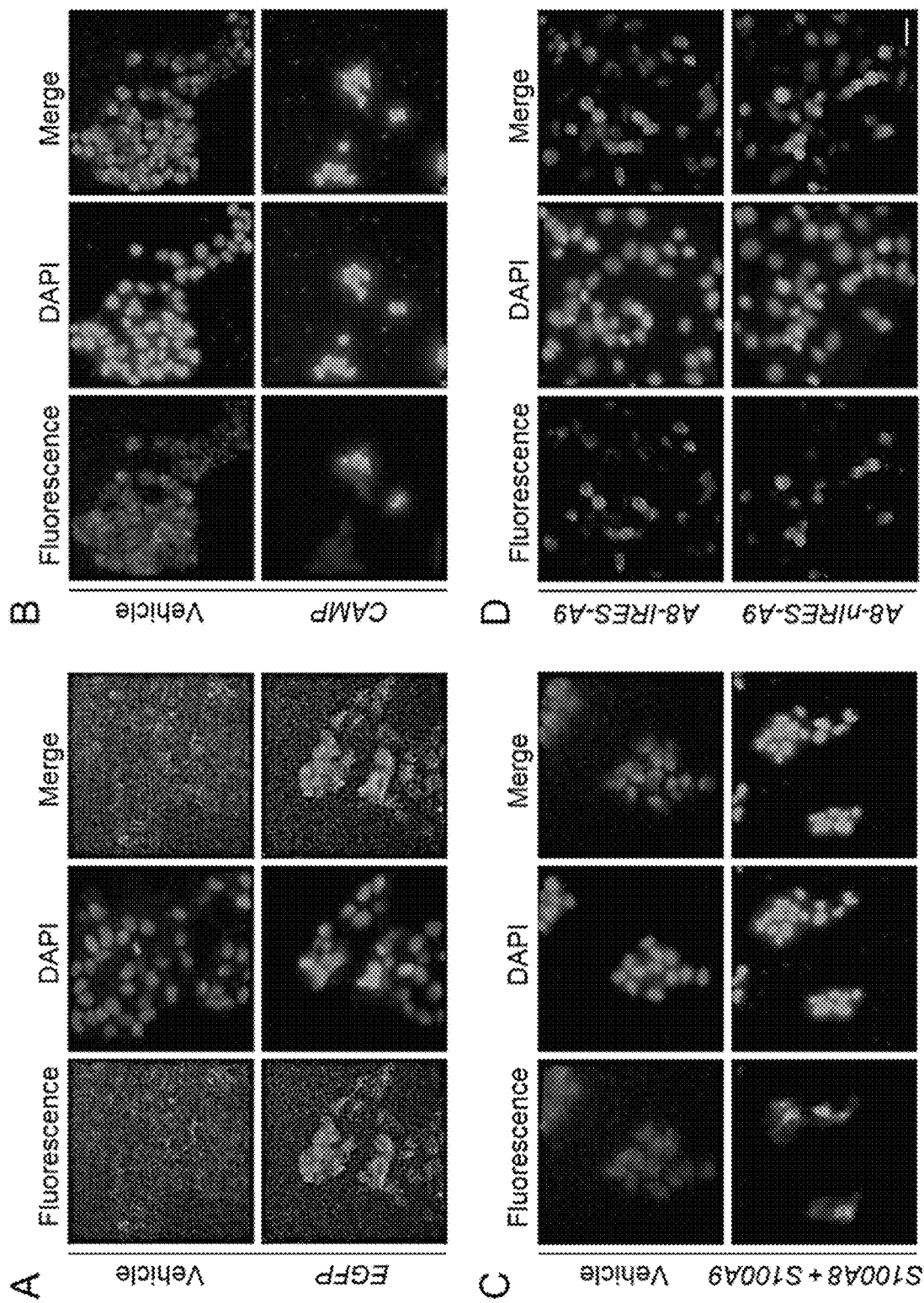
FIG. 6. Protein expression after mRNA transfection. Immunofluorescent microscopy images of (A) EGFP mRNA transfection for 16 hours. (B) CAMP mRNA transfection for 16 hours. (C) S100A8/S100A9 mRNA (mol/mol=1:1) cotransfection for 16 hours, (D) A8-IRES-A9 and A8-nIRES-A9 mRNA transfection for 40 hours. Vehicle, PBS. Bar=10 μM. The experiments were performed three times and representative images are shown.

Following mRNA transfections, CAMP and calprotectin were also detected in KB cells using immunofluorescence. Endogenous CAMP, S100A8, and S100A9 protein levels are at or below the limits of detection and fluorescence above background was not detected with mock transfections (FIG. 6). At 16 hours after delivery of mRNAs for EGFP, CAMP, or calprotectin (S100A8/S100A9), significant fluorescence was detected, suggesting mRNA delivery increases EGFP, CAMP, and calprotectin protein expression (FIG. 6A, 6B, 6C). At 16 hours after transfection with A8-IRES-A9 and A8-nIRES-A9 mRNAs, no significant fluorescence was detected (data not shown). At 40 hours following mRNA transfection, however, fluorescence signals were detected for calprotectin (FIG. 6C). These results are consistent with the western blot analysis (FIG. 1B, FIG. 2D, 2E).

CAMP or Calprotectin mRNA Transfection Increases Resistance of KB Cells to Bacterial Invasion We determined whether select antimicrobial proteins produced after mRNA transfections into epithelial cells affected resistance to invasion by bacterial pathogens. Following transfection with all CAMP and calprotectin mRNA constructs, resistance of epithelial cells to invasion by *Listeria* and *Salmonella* was significantly increased at eight hours (FIG. 3A), 24 hours (FIG. 3B), and 48 hours (FIG. 3C). Resistance seemed to be greatest at 8 h after transfection. The CAMP and S100A8+S100A9 mRNA transfection schemes appeared to increase resistance more effectively than the tandem mRNA constructs. The tandem constructs, however, contained fewer molar equivalents of S100A8 and S100A9 mRNAs than S100A8+S100A9. Hence, the tandem constructs may be as effective as co-transfection.

The TransIT-mRNA Delivery System Reduces Cell Viability without Triggering Apoptosis.

Figure 4:
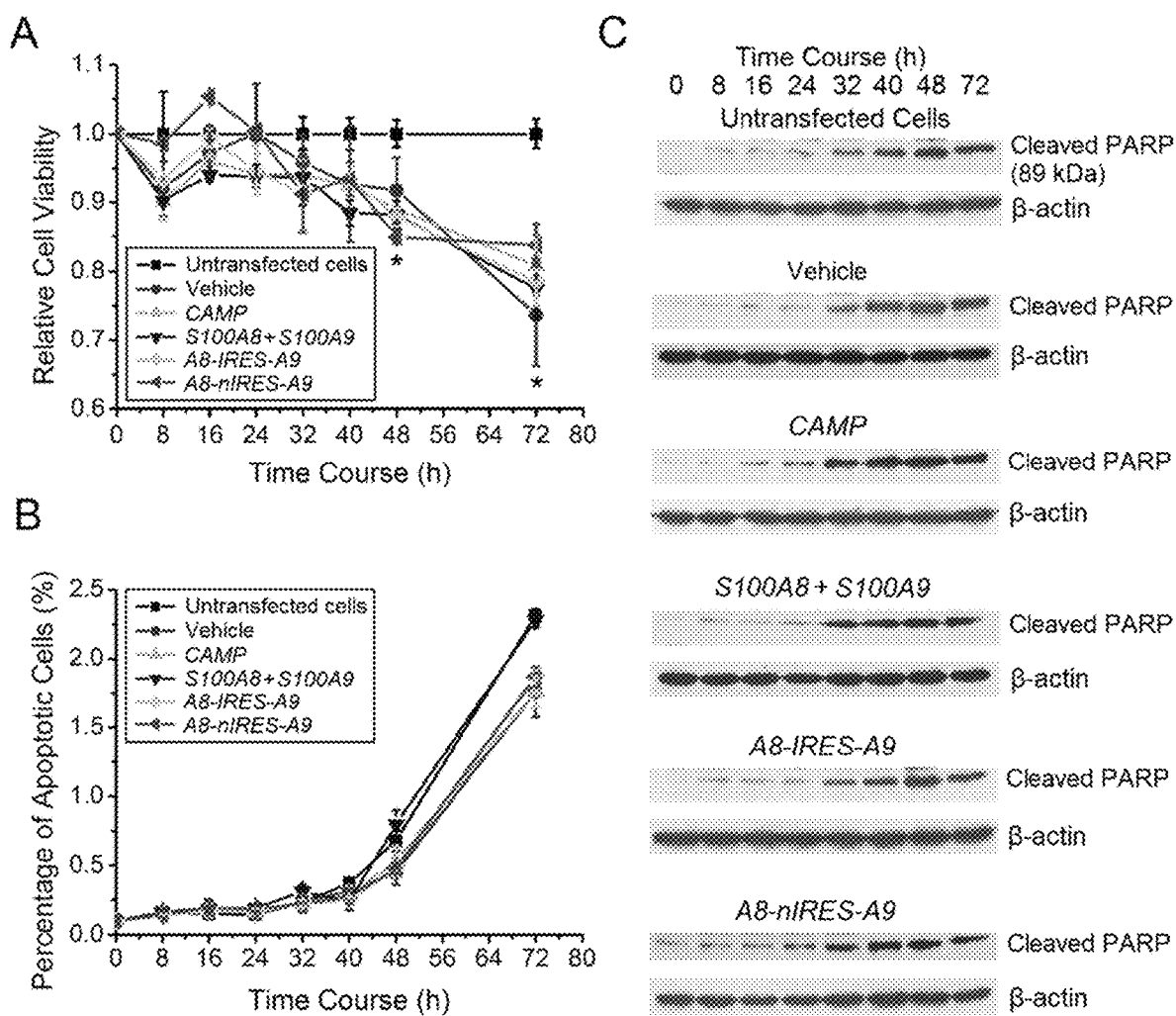
FIG. 4. The mRNA delivery reduces cell viability without triggering apoptosis. (A) Cell viability was determined using the MTT assay at the times indicated for three days after mRNA delivery of mRNA constructs to KB cells. PBS-mock-transfected cells were used as a control, with their viability set at 1. Each experiment was done in triplicate and repeated at least twice. (B) Analysis of apoptotic cells using Western blots after mRNA delivery of mRNA constructs. Cells that were positively stained by annexin-V-FITC using flow cytometry were considered apoptotic. In panels A and B, error bars show the means±SD or three to six independent experiments. *p<0.05. C. Western blot analysis for PARP cleavage after delivery of mRNA constructs. PBS-mock-transfected (vehicle) cells and untransfected cells were used as controls.

Cytolethality of these mRNAs delivered by TransIT-mRNA transfection reagent was analyzed by measuring cell viability using MTT assay and by quantifying apoptotic cells via flow cytometry and PARP-cleavage. When compared with untransfected cells, transfection of cells with vehicle, CAMP, S100A8/S100A9, A8-IRES-A9, or A8-nIRES-A9 mRNAs significantly reduced cell viability 48 hours and 72 hours later (FIG. 4A). When compared to untransfected cells, delivery of the vehicle, CAMP, S100A8/S100A9, A8-IRES-A9 or A8-nIRES-A9 mRNAs did not affect apoptosis (FIG. 4B). The small increment in apoptotic cells at 72 hours after each of the transfections was indistinguishable from untransfected cells. Further analysis of the apoptotic status of the KB cells used western blot analysis for poly (ADP-ribose) polymerase (PARP) cleavage, an indicator of caspase activation (Taylor et al., 2008. *Nature Rev. Mol. Cell Biol.* 9: 231-241). PARP cleavage was elevated 32 hours after mRNA transfection (FIG. 4C). When compared to the untransfected cells, the pattern of cleaved PARP after delivery of the mRNAs was similar (FIG. 4C).

We show for the first time that epithelial cell resistance to invasive pathogens in vitro can be augmented by transient transfection using mRNAs encoding antimicrobial CAMP and calprotectin (S100A8/S100A9, A8-IRES-A9 and A8-nI-RES-A9). Gene transfer vehicles with mRNA cargo appear to be attractive alternatives to vehicles delivering DNA for the treatment of disease despite persistent concerns that the ease of synthesis and stability of transfected mRNA would prove insufficient to yield a useful protein product (Tavernier et al., 2011. *J. Control. Release*. 150: 238-47). mRNA delivery facilitates simultaneous expression of all epitopes of an antigen and manipulation and purification is rather simple.

When we consider this approach for development of potential therapeutic agents on mucosal or epidermal surfaces or into accessible tissues, mRNA delivery has several advantages over DNA gene transfer techniques. Since mRNA does not integrate into the genome and the transfection remains transient, the pharmaceutical safety of mRNA transfection is greater than for DNA gene transfer therapy. With the goal of developing a therapeutic that augments mucosal immunity, we show for the first time the delivery of in vitro transcribed, capped, and polyadenylated mRNAs specifying antimicrobial protein into human epithelial cells and the corresponding functional effects.

Stability of the mRNA cargo synthesized by in vitro translation improved through 5' capping with anti-reverse cap analogue (ARCA), and protein expression can be increased by 3' mRNA capping using poly(A) chains in cis and in trans (Mockey et al., 2006. *Biochem. Biophys. Res. Commun*. 340: 1062-1068). Thus, certain mRNA modifications improve the stability of the mRNA. Nevertheless, the specific mRNA cargo, the stability of the translated protein, and the target cell all affect the kinetics and efficiency of new protein expression.

In our studies, different mRNAs were compared. CAMP, S100A8 and S100A9 protein peaked 16 hours after mRNA transfection (FIG. 1B, 2A, 2B). After S100A8/S100A9 mRNA cotransfection, S100A8 and S100A9 proteins peaked at 24 hours and declined slowly when compared to single transfections with S100A8 or S100A9 mRNA (FIG. 2C). Since S100A8 and S100A9 spontaneously form heterodimers (Hsu et al., 2009. *Antiinflamm. Antiallergy Agents Med. Chem*. 8: 290-305), dimerization after co-transfection is suggested to inhibit degradation of each subunit.

Calprotectin, the heterodimeric complex of S100A8 and S100A9, increases innate immunity of the cytoplasm of epithelial cells increasing resistance against invading bacteria including *Listeria* spp. and *Salmonella* spp. Co-transfection with both the S100A8 and S100A9 mRNAs induced production of S100A8/A9 in the KB cells (FIG. 6C). To simplify the transfection process for translation of calprotectin, we used pIRES to construct a mammalian expression vector that allows high level expression of two genes from the same bicistronic mRNA transcript. The vector contains the encephalomyocarditis virus (ECMV) internal ribosome entry site (IRES) flanked by two multiple cloning sites (MCS A and B) (Bochkov et al., 2006. *Biotechniques* 41: 283-284, 286, 288). The first cistron is translated by the cap-dependent scanning mechanism, whereas the second cistron is translated by the cap-independent IRES element initiation mechanism (Bochkov et al., 2006. *Biotechniques* 41: 283-284, 286, 288). pIRES contains a partially disabled IRES sequence that reduces the rate of translation of the gene cloned into MCS B in comparison to MCS A (Rees et al., 1996. *Biotechniques* 20: 102-110). To facilitate translation of calprotectin from a single transfection construct, S100A8 and S100A9 ORFs were cloned into a pIRES vector and the plasmid was transfected into KB cells. Using cDNA cloned in tandem with pIRES, formation of calprotectin (S100A8/S100A9 dimers) can be observed (Champaiboon et al., 2009. *J. Biol. Chem*. 284:7078-90). When we cloned the tandem mRNAs with pIRES, calprotectin dimers were also seen (FIG. 6D) and the signals were similar to co-transfection with S100A8 and S100A9 mRNAs (FIG. 6C).

Since the S100A9 mRNA cloned into the MCS B site with pIRES was expected to show attenuated translation, we also constructed a vector with a native (n, non-attenuated) IRES. Calprotectin protein expression with pIRES and nIRES was similar (FIG. 6D, top and bottom; FIG. 2D, 2E). Since equal concentrations of mRNA vectors were delivered to the cells, the tandem constructs would appear to translate more efficiently than S100A8 or S100A9 alone but no quantitative comparisons can be made. Likewise CAMP mRNA transfection and translation was also successful but we cannot compare the efficiency to calprotectin. It is clear, however, that S100A8 and S100A9 protein expression was more stable when co-transfected or when A8-IRES-A9 or A8-nIRES-A9 mRNAs were delivered (FIG. 2D, 2E). The several constructs for S100A8/S100A9, A8-IRES-A9 and A8-nIRES-A9 mRNAs resulted in different kinetics of translation and it is apparent that the MCS B site insert proximal to pIRES (FIG. 2D) and nIRES (FIG. 2E) showed a delay. Without wishing to be bound by any particular theory, the mRNAs in the MCS B site may be scanned and translation initiated by a low efficiency, cap-independent IRES mechanism in KB cells.

Our results showed that half-lives of ARCA capped CAMP, S100A8/S100A9, A8-IRES-A9, and A8-nIRES-A9 mRNAs following transfection in KB cells were between eight hours to 16 hours (FIG. 6A-D). To increase the half-lives, these mRNA constructs included two sequential human beta-globin UTRs. Differences in stability of these transfected mRNAs might be due the mRNA secondary structures, which can affect recognition by RNA degradation enzymes and ancillary proteins associated with regulation of RNA degradation. Whereas differences in mRNA in half-life may reflect the proportion of pools sequestered or exposed to cytoplasmic degradation and translation after liposome delivery (Barreau et al., 2006. *RNA* 12: 1790-1793), this phenomenon is unlikely to explain our results. Our transfections used a commercially available non-liposomal, cationic polymer/lipid formulation (TransIT®-mRNA Transfection Kit, Minis Bio LLC, Madison WI). Although mRNAs with premature stop codons can prevent translation of full-length messages and prevent the production of full-length proteins via the nonsense-mediated decay pathway (Apcher et al., 2011. *Proc. Natl. Acad. Sci. USA.* 108: 11572-11577), it is unclear whether this mechanism can explain variability in mRNA half-lives and protein translation in our cells.

As is described in more detail below, an mRNAs may be constructed to include one or more modified bases. Such modified mRNAs may exhibit increased stability and/or reduced potential for immune responses (Kormann et al, 2011, *Nat Biotechnol* 29(2):154-157).

Ultimately, the test for mRNA transfection efficiency is new or augmented function and minimal associated cytotoxicity or induction of apoptosis. Our data showed that either CAMP or calprotectin mRNA delivery could significantly increase resistance of epithelial cells to invasion by *Listeria* and *Salmonella* (FIG. 3A-3C). To perform these experiments, we reconciled differences in cell confluence needed for optimal use of the TransIT-mRNA transfection reagent (60-90%), with the 40-60% cell confluency for optimal performance of the antibiotic protection assay (Champaiboon et al., 2009. *J. Biol. Chem.* 284:7078-90; Nisapakultorn et al., 2001. *Infect. Immun.* 69: 4242-4247; Nisapakultorn et al., 2001. *Infect. Immun.* 69, 3692-3696). To perform the antibiotic protection assay after optimal transfection, cells were split at eight hours and 32 hours following transfection and then cells were incubated for another 16 hours to adjust cell confluency to 40% to 60% for bacterial invasion Antimicrobial activity at 24 hours and 48 hours following mRNA transfection was lower than at eight hours following transfection (FIG. 3A-3C); cell division over time (and subculturing) decreased intracellular CAMP or calprotectin protein levels. Nonetheless, the residual LL-37 and calprotectin levels were sufficient to provide statistically significant increases in resistance to the invading pathogens up to 48 hours after transfection.

Figure 3:
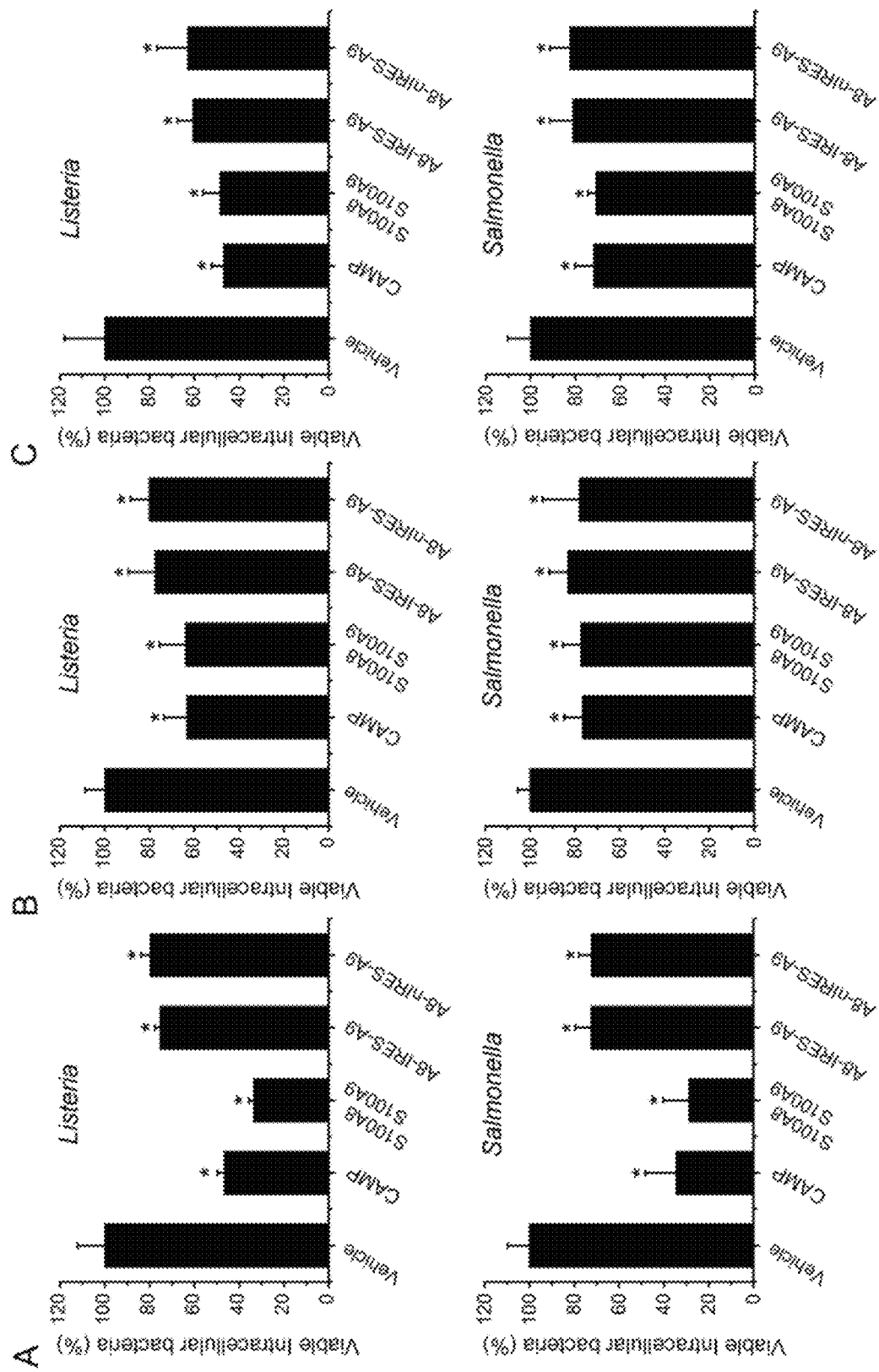
FIG. 3. CAMP and calprotectin mRNAs increase resistance to *Listeria* and *Salmonella* invasion. Monolayers were transfected with mRNAs for (A) eight hours, (B) 24 hours, (C) 48 hours, and then incubated for two hours with *L. monocytogenes* ATCC 10403 S at MOI 100:1 or *S. typhimurium* ATCC 14028 at MOI 1:1. After 24-hour or 48-hour transfection, cells were split at eight hours and again 32 hours later, then incubated for another 16 hours. Viable intracellular bacteria are reported as percentage mean±SD expressed relative to the CFUs in KB cells mock-transfected with vehicle (PBS), which is set to 100%. Error bars show the means±SD relative to the eight-hour vehicle control for three to six independent experiments. *$p<0.05$.

We found no evidence to indicate that mRNA delivery of any of the cargo mRNAs or their translated protein products induced apoptosis. Since the vehicle control showed similar viability reductions as the mRNA delivery, we concluded that the small loss of viability over time was attributable to the TransIT-mRNA delivery system rather than protein expression. When compared with untransfected cells, antimicrobial protein mRNA (CAMP, S100A8/S100A9, A8-IRES-A9, and A8-nIRES-A9) delivery and intracellular protein production did not significantly trigger apoptosis. Taken together, the data suggest that the TransIT-mRNA delivery system reduces cell viability but does not trigger apoptosis. The loss in viability with this reagent is not considered to be consequential in vivo. Systemic administration does not cause immune cell activation (Karikó et al., 2011. *Nucl. Acids Res.* 39: e142) and this reagent appears to be less toxic and shows greater transfection efficiency than electroporation (Gonzalez et al., 2007. *J. Virol. Methods.* 145: 14-21). Most importantly, loss of cell viability resulting from transfection did not appear to affect invasion data since the apoptosis results were similar with the vehicle control (FIG. 3, 4A). These data show that an mRNA delivery system can be an effective surrogate for a DNA gene therapy approach for treatment or control of mucosal infections. Use of this approach for therapeutic purposes in mucosal infections may be enhanced with a mRNA packaging system that would increase mRNA stability, minimize immune activation, and/or more specifically target mucosal epithelial cells.

The presence of saliva on the surfaces of oral mucous membranes could be a barrier to topical mRNA transfections for therapeutic purposes. Saliva contains high molecular mass mucins and many other proteins that could form a diffusion barrier at the surface of epithelial cells in the mouth. In addition, saliva contains RNases, which could degrade the therapeutic mRNAs.

To test this possibility, we added saliva to target epithelial cells in vitro, attempted to transfect with EGFP mRNA, and tested for translation of EGFP by the emission of green fluorescence. We also modified the nucleotide composition of the mRNA to increase its stability and reduce potential immunogenicity (Kormann et al, 2011, *Nat Biotechnol* 29(2):154-157). The modification replaces 25% of the cytidine with methylcytidine and 25% of the uridine with 2-thiouridine. Adenine and guanosine remain unchanged.

Figure 15:
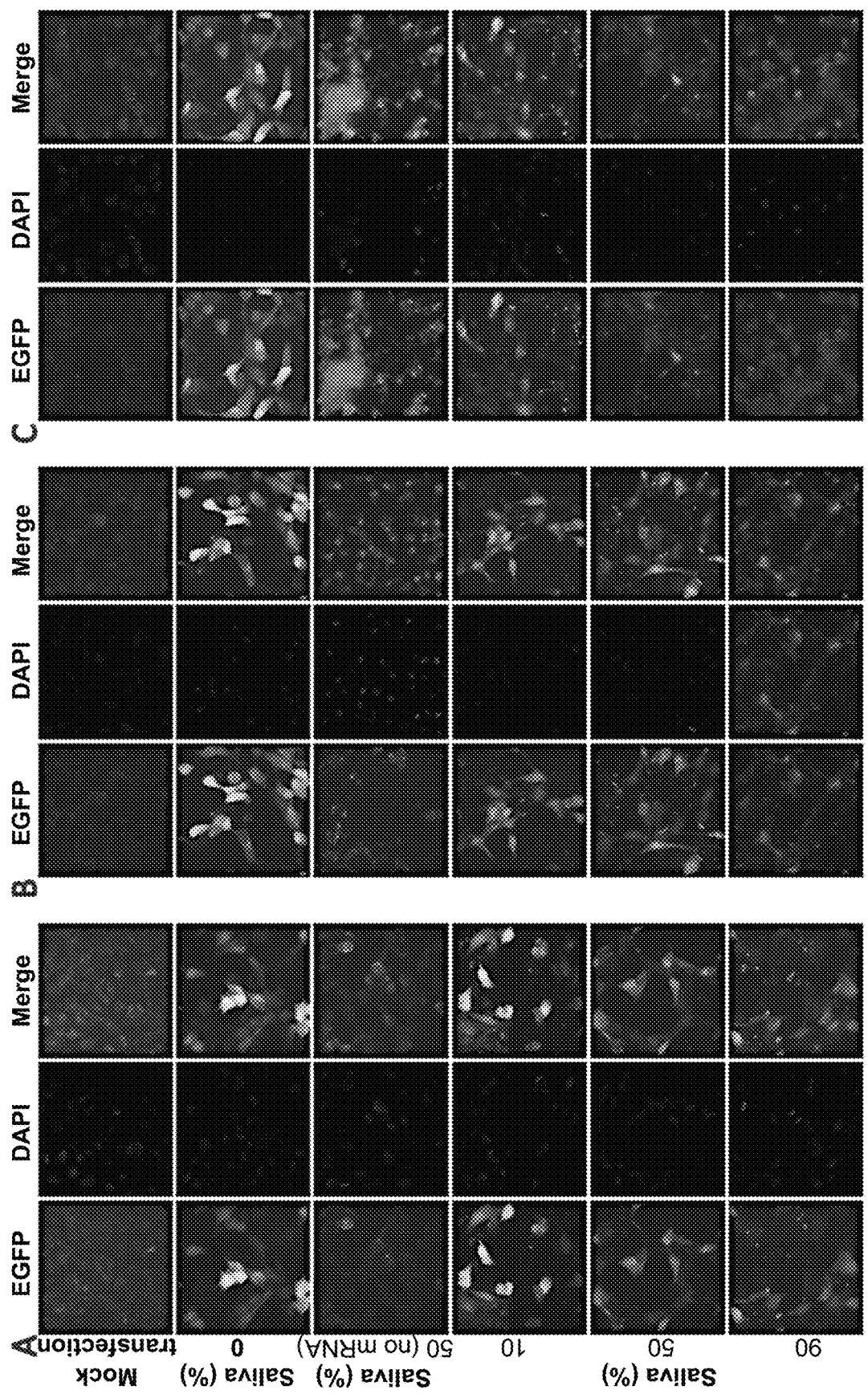
FIG. 15. Effects of saliva concentration and treatment time on EGFP mRNA delivery into KB cells. Cells were incubated at 37° C. with 10%, 50% or 90% saliva for (A) one minute, (B) three minutes, or (C) five minutes, washed three times with fresh medium, and then incubated with packaged, modified mRNA encoding EGFP. Cells treated with 50% saliva but without mRNA delivery were used as control.
Figure 16:
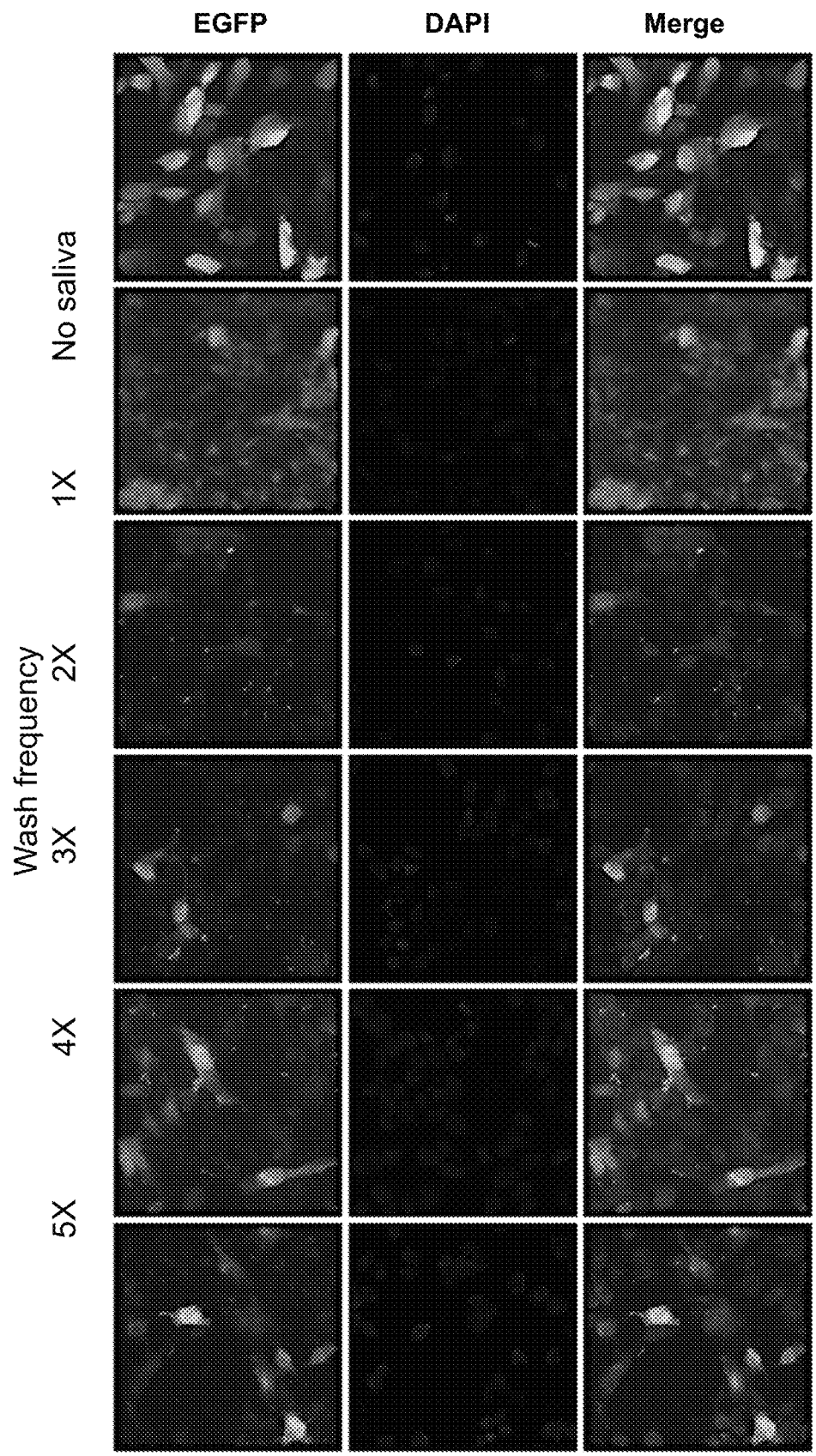
FIG. 16. EGFP mRNA delivery into KB cells: effects of wash frequency to reverse effects of saliva treatment. Cells were treated with 90% saliva for three minutes, washed for the indicated frequencies with fresh medium, followed by mRNA transfection.

In the absence of added saliva (0% saliva), the transfected epithelial cells produced EGFP; without transfection no green fluorescence was seen with or without saliva (FIG. 15 A-C). Pretreating the cells with increasing amounts of saliva for increasing amounts of time (up to five minutes) abrogated production of green fluorescence. Washing cells with fresh culture medium with increasing repeat frequency (up to five washes) reversed the inability of the mRNA transfection to produce green fluorescence (FIG. 16). Washing the cells five times maximized the recovery of successful mRNA transfection, although the efficiency was less than in the absence of saliva.

Washing saliva-treated epithelium in vitro reversed the inhibition of the mRNA transfection approach. In the clinical setting, washing mucosal epithelium and preventing re-exposure to saliva can help overcome the salivary barrier to transfection and increase transfection efficiency. Moreover, saliva is a representative model of mucosal fluids, particularly with respect to composition and viscosity. Thus, the saliva wash results shown in FIG. 15 and FIG. 16 indicate that pretreatment of a mucosal surface by washing mucosal fluids from the surface can increase the transformation efficiency of other mucosal epithelia such as, for example, mucosal epithelia of the genitourinary system, eyes, or other squamous mucosae.

We also present data supporting the use of mRNA transfection to express a complex of two proteins (which are antimicrobial) that can be tumor suppressive if inoculated directly into epithelial cancers such as, for example, cervical cancers and cancers of the head and neck. (Khammanivong et al., 2013. *PLoS One* 8:e69395. Doi: 10.1371/journal.pone.0069395). Loss of growth suppression is one of the hallmarks of cancer (Hanahan and Weinberg, 2011. *Cell* 144: 646-674), contributing to malignant transformation and tumorigenesis. The molecular mechanisms leading to abnormal cell cycle regulation and growth vary in different types of cancer and remain elusive in head and neck squamous cell carcinoma (HNSCC). Calprotectin may be involved in growth regulation and tumorigenesis in HNSCC and other squamous cell carcinomas (SCCs). S100A8/A9 is constitutively expressed in the cytoplasm of healthy squamous epithelial cells of the oral cavity and oropharynx (Ross et al., 2001. *Infect Immun* 69: 3248-3254; Hitomi et al., 1998. *Arch Histol Cytol* 61: 163-178). Encoded by coding regions that map to human epithelial differentiation complex on chromosomal locus 1q21, S100A8 and S100A9 are members of the S100 family of proteins, which contain two canonical EF-hand calcium-binding motifs involved in calcium-dependent control of cell differentiation, cell cycle progression and growth (Itou et al., 2002. *J Mol Biol* 316: 265-276), and are implicated in cancer development and other inflammatory diseases. In cancer, extracellular S100A8/A9, typically released from the cytoplasm of infiltrating polymorphonuclear leukocytes and macrophages (Hessian et al., 2001. *Eur J Biochem* 268: 353-363; Hsu et al., 2009. *Antiinflamm Antiallergy Agents Med Chem* 8: 290-305), is associated with inflammation and progression of the disease (Gebhardt et al., 2002. *Oncogene* 21: 4266-4276). When released, S100A8/A9 can signal through the receptor for advanced glycation end products (RAGE) and/or toll-like receptor 4 (TLR4) to promote tumor-associated inflammation and progression of advanced stage adenocarcinomas and colitis-associated cancer (Hermani et al., 2006. *Exp Cell Res* 312: 184-197; Gebhardt et al., 2006. *Biochem Pharmacol* 72: 1622-1631; Ehrchen et al., 2009. *J Leukoc Biol* 86: 557-566; Turovskaya et al., 2008. *Carcinogenesis* 29: 2035-2043). Little is known, however, about the intracellular roles of S100A8/A9 and how the protein complex regulates functions in cancer cells.

Expression of intracellular S100A8/A9 appears to be cell- and tissue-specific and may be differentially regulated in different malignancies. S100A8/A9 levels can be abnormally elevated in human primary tumors originating from tissues that do not normally express the protein, such as the skin (Gebhardt et al., 2002. *Oncogene* 21: 4266-4276), breast (Arai et al., 2008. *Curr Cancer Drug Targets* 8: 243-252; Moon et al., 2008. *Mol Cancer Res* 6: 1544-1553), thyroid (Ito et al., 2009. *Anticancer Res* 29: 4157-4161), liver (Nemeth et al., 2009. *Hepatology* 50: 1251-1262), gastric mucosa (Yong et al., 2007. *Arch Pharm Res* 30: 75-81), prostate (Hermani et al., 2006. *Exp Cell Res* 312: 184-197), ovary (Odegaard et al., 2008. *Am J Obstet Gynecol* 198: 418 e411-417), bladder (Yao et al., 2007. *Anticancer Res* 27: 3051-3058) and lung (Arai et al., 2001. *Oncol Rep* 8: 591-596). In these tissues, whether increased S100A8/A9 level is a response to tumorigenesis or actually drives tumor development and progression is unclear. In contrast, S100A8/A9 expression can decrease in human tumors of squamous epithelial cell origin that normally express the protein complex constitutively, such as head and neck (including oral, nasopharyngeal and oropharyngeal) (Melle et al., 2004. *Cancer Res* 64: 4099-4104; Gonzalez et al., 2003. *Arch Otolaryngol Head Neck Surg* 129: 754-759; Fung et al., 2000. *Life Sci* 67: 923-936), esophageal (Kong et al., 2004. *World J Gastroenterol* 10: 1093-1097; Wang et al., 2004. *Cell Res* 14: 46-53) and cervical (Tugizov et al., 2005. *J Virol* 79: 1099-1112; Coleman et al., 1994. *Hum Pathol* 25: 73-79) SCCs. In these squamous epithelial cancers, decreased S100A8/A9 correlates with loss of differentiation and increase in growth and invasiveness. Conversely, S100A8/A9-expressing SCCs appear less aggressive. We sought to determine, therefore, whether S100A8/A9 functions as a growth regulating factor in SCCs.

To test the regulatory role of S100A8/A9 by rescue in S100A8/A9-negative carcinoma cells, we stably transfected KB cells to express S100A8/A9 protein complex. Stable expression of S100A8/A9 in KB cells results in S100A8/A9-dependent G2/M cell cycle arrest and reduced anchor-age-independent growth and colony formation in soft agar. To determine the effect of reducing S100A8/A9 levels, S100A8 and S100A9 were silenced in the TR146 cells using short hairpin RNA (shRNA). In TR146 cells, silencing S100A8 and S100A9 expression reverses the suppressive effect on growth and clonogenicity and appears to be associated with the loss of G2/M checkpoint control. Both G1/S and G2/M cell cycle checkpoints are dysregulated in carcinomas, leading to uncontrolled cell growth and proliferation. Growth regulation by S100A8/A9 in KB cells was not found to be through G1, G1/S checkpoint or S phase. Instead, S100A8/A9 expression increases protein phosphatase 2A (PP2A) activity, apparently through protein-protein interaction, which appears to be involved in modulating and restoring G2/M checkpoint signaling and reduction of carcinoma growth.

PP2A is a serine and threonine (Ser/Thr) protein phosphatase known to regulate cell cycle checkpoint by targeting G2/M-specific Cdc25C for inactivation by dephosphorylation at Thr48, inhibiting the mitotic exit, and cell division (Forester et al., 2007. *Proc Natl Acad Sci USA* 104: 19867-19872; Margolis et al., 2006. *Cell* 127: 759-773). PP2A targets a broad spectrum of phosphoproteins and has also been shown to exert anti-tumor activities by inhibiting AKT and C-MYC in the cell survival and proliferation pathways and by inducing cell cycle arrest (Guenin et al., 2008. *Int J Oncol* 32: 49-57). When interacting with S100A8/A9 [B30], PP2A may be activated to exert regulatory roles in cell cycle progression at the G2/M checkpoint. S100A8/A9 and PP2A may therefore function as interacting partners to regulate mitosis and control cellular growth. Reduction in S100A8/A9 in carcinomas (in HNSSC for example) may lead to a diminished PP2A phosphatase activity and increased growth and tumorigenesis.

S100A8 and S100A9 Gene Expression by qRT-PCR in Normal and SCC Samples

Figure 7:
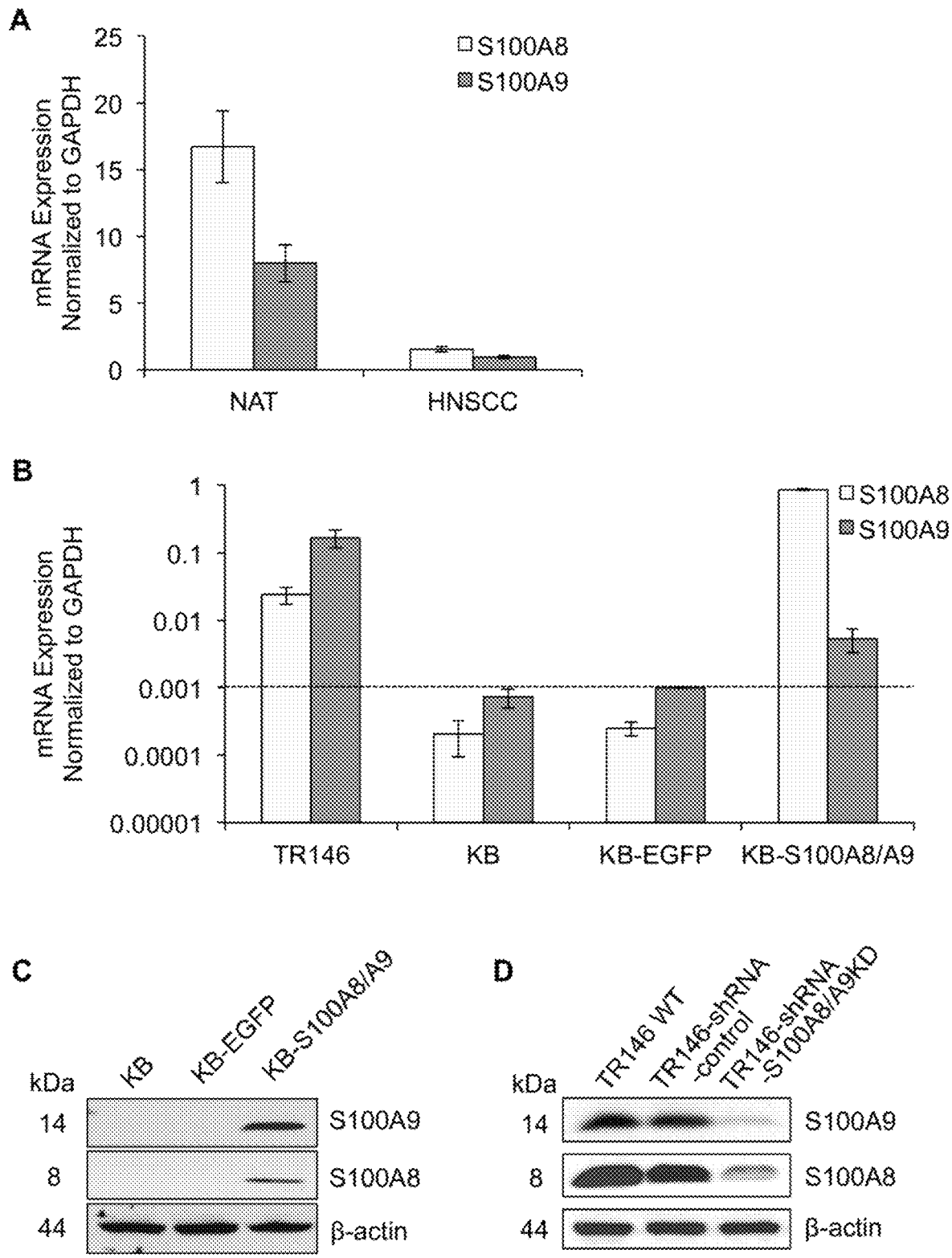
FIG. 7. Expression of S100A8 and S100A9 in human head and neck tissues and carcinoma cell lines. The mRNA expression levels of S100A8 and S100A9 in (A) normal adjacent (NAT) and HNSCC tissues and (B) TR146 HNSCC and KB cells were measured by qRT-PCR and normalized to GAPDH; dotted line shown as a threshold for detection. Total RNA extracted from matching NAT and HNSCC tissues from each of three patients was pooled separately for gene expression analysis. Cell lines cultured under standard conditions were harvested and analyzed at approximately 70% confluency. Data presented as mean±SD (n=2). Representative immunoblots of (C) S100A8 and S100A9 in KB-S100A8/A9 transfected cells and (D) TR146-shRNA-S100A8/A9 knockdown cells compared to wild type and negative transfection controls. β-actin was used as loading control for immunoblotting analysis separated in 10% SDS-PAGE gels.

S100A8/A9 protein expression is reduced in HNSCC (Driemel et al., 2007. *Proteomics Clin Appl* 1: 486-493;

Roesch et al., 2005. *Eur J Cell Biol* 84: 431-444). We compared the expression of S100A8 and S100A9 subunit genes in matching HNSCC and normal adjacent (NAT) tissues using real-time quantitative reverse-transcription polymerase chain reaction (qRT-PCR). Expression analysis was normalized to GAPDH housekeeping gene as an internal and total RNA loading control. Total RNA from HNSCC and NAT tissues were pooled separately from three different patients with stage II, III and IVA tumors and analyzed for differential mRNA expression. Using qRT-PCR, we found that S100A8 and S100A9 expression was approximately 10-fold lower in HNSCC than NAT as normal tissue control (FIG. 7A).

We have also investigated the level of S100A8 and S100A9 expression in over 35 clinical cases of HNSCC and eleven healthy oral mucosal samples using microarray gene expression profiling and found that expression of these proteins was also depressed relative to normal control tissues (unpublished data). Expression of S100A8 and S100A9 in TR146 and KB-S100A8/A9 cells was approximately one- to two-log-fold greater than in S100A8/A9-negative KB and KB-EGFP cells (FIG. 7B; dotted line shown as a threshold for detection). KB-S100A8/A9 cells are S100A8/A9-negative KB cells transfected to over-express S100A8/A9, whereas KB-EGFP cells are sham-transfected controls. In KB wild-type and sham-transfected KB-EGFP cells, S100A8 and S100A9 mRNA and protein expression was barely detectable, whereas transfected KBS100A8/A9 and TR146 cells clearly showed S100A8 and S100A9 protein expression (FIG. 7C, 7D). S100A8-specific and S100A9-specific stable shRNA transfection of TR146 cells reduced endogenous S100A8 and S100A9 proteins to barely detectable levels (FIG. 7D). S100A8 and S100A9 protein levels appear to differ as shown by immunoblotting (FIG. 7C, 7D). Such differences may be real or reflect differences in the sensitivity of the primary antibodies used. Hence, the levels of S100A8 and S100A9 could not be directly compared to one another.

Anchorage-Dependent and -Independent Growth of Carcinoma Cells Suppressed by S100A8/A9

Figure 8:
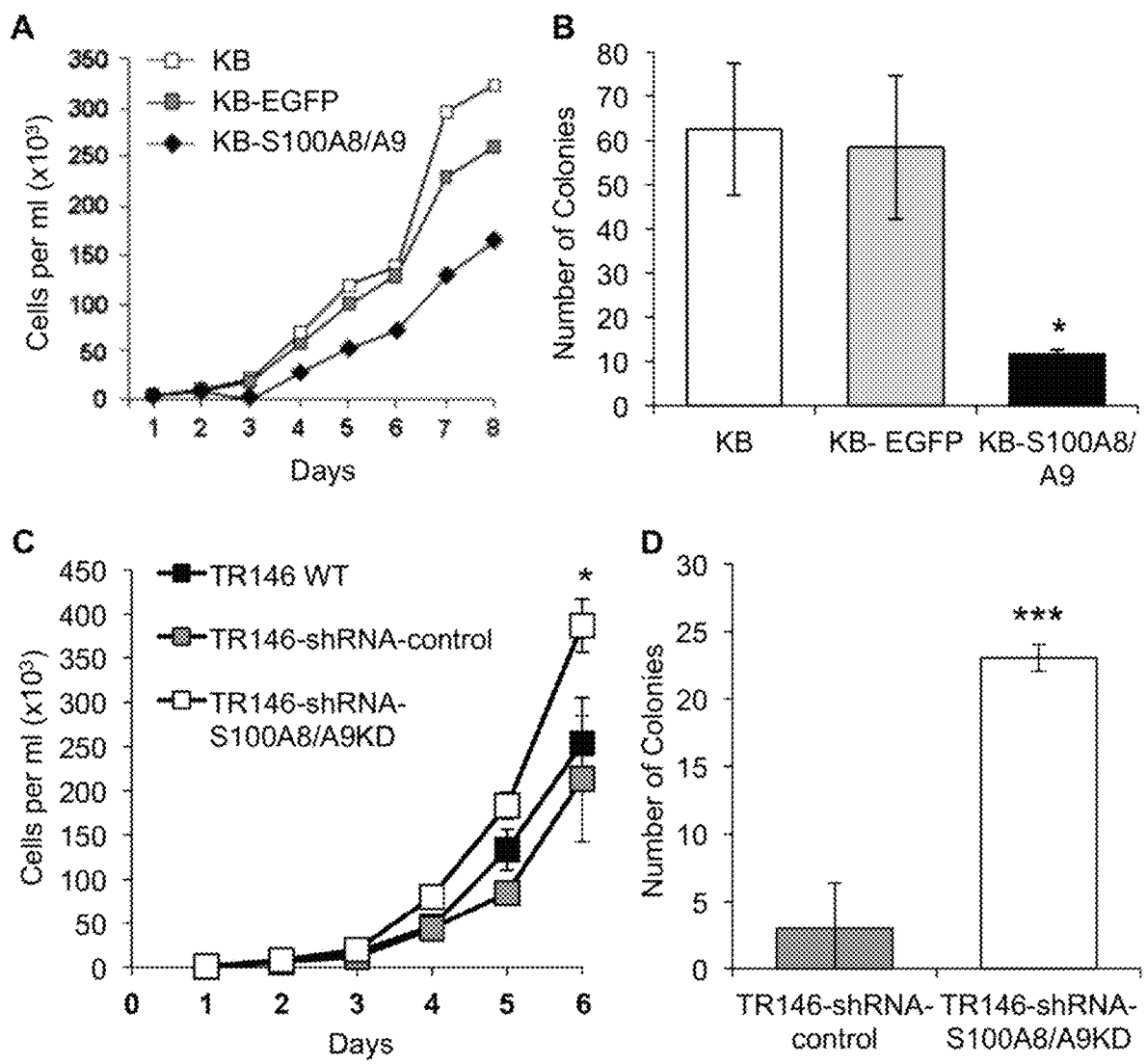
FIG. 8. S100A8/A9 suppressed anchorage-dependent and anchorage-independent growth of KB cells. (A) Growth curves of KB-S100A8/A9 cells compared to KB-EGFP and KB wild-type control cells. Cells were grown on non-pyrogenic polystyrene tissue flasks in fresh MEM supplemented with 10% FBS every three days. (B) Anchorage-independent growth in soft agar for KB, KB-EGFP and KB-S100A8/A9 cells (mean±SEM, *p<0.03, n=4). (C) Anchorage-dependent growth on tissue flasks in complete medium (mean±SD, *p<0.02, n=3) and (D) colony formation in soft agar (mean±SEM, ***p<0.0005, n=2) of TR146-shRNAS100A8/A9KD cells compared to TR146 WT and TR146-shRNA-control cells.

The ability of S100A8/A9 to regulate cell growth was tested in transfected KB-S100A8/A9 cells on standard non-pyrogenic polystyrene tissue culture flasks for anchorage-dependent (adherent) and in soft agar for anchorage-independent growth conditions. Highly malignant cells are able to survive, form colonies, and proliferate independent of anchorage and are routinely tested in soft agar. When compared to KB wild-type or KB-EGFP cells, KBS100A8/A9 cells showed approximately two-fold lower anchorage-dependent growth in vitro (FIG. 8A). Ectopic expression of S100A8/A9 did not appear to induce apoptosis in KB-S100A8/A9 cells when grown under standard adherent conditions, since neither cleaved caspase 1 nor cleaved caspase 3 was detectable by immunoblot, whereas KB wild-type, KB-EGFP and KB-S100A8/A9 cells showed similar total caspase 1 and caspase 3 levels (data not shown). During anchorage-independent growth in soft agar, KB-S100A8/A9 cells grew poorly, forming smaller and fewer colonies than KB and KB-EGFP cells (FIG. 8B). To confirm the effect of S100A8/A9 on cell growth, knockdown of endogenous S100A8/A9 expression in TR146-shRNA-S100A8/A9KD cells showed increased anchorage-dependent (FIG. 8C) and anchorage-independent (FIG. 8D) growth in comparison to knockdown-negative control cells (TR146-shRNA-control).

S100A8/A9 Induces G2/M Cell Cycle Checkpoint Arrest

Figure 9:
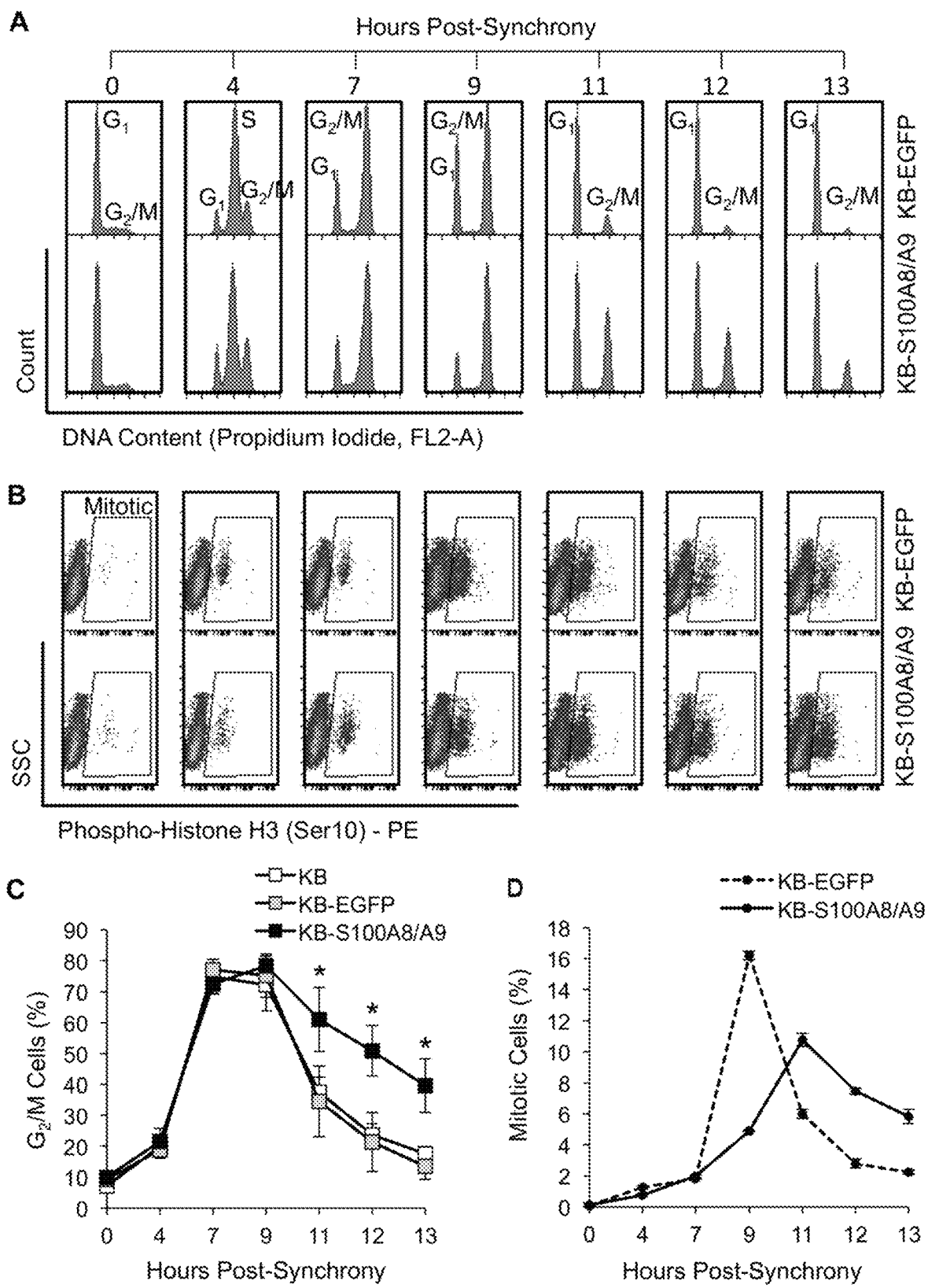
FIG. 9. S100A8/A9 expression induced cell cycle and mitotic arrest at G2/M. (A) Cell cycle analysis of KB, KB-EGFP and KB-S100A8/A9 cells post-synchrony. Cells cultured under standard conditions were serum-starved overnight, synchronized at G1/S with aphidicolin treatment and stimulated to re-enter cell cycle. Synchronized cells were stained with propidium iodide DNA staining solution and analyzed by flow cytometry for changes in DNA content following release from G1/S blockage. (B) Mitotic analysis of synchronized cells stained with phospho-Histone H3 (Ser10) and analyzed by flow cytometry. (C) Percentage of cells in G2/M. KB, KB-EGFP and KB-S100A8/A9 cells were analyzed over time post-synchrony and reported as mean±SEM; n=2 independent experiments (each analysis performed in duplicate); *p<0.05. (D) Percentage of mitotic cells post-synchrony, representing the mean of two independent repeat experiments. KB-S100A8/A9 cells showed fewer mitotic cells as shown by lower phospho-Histone H3 (Ser10) staining.

To determine whether S100A8/A9 suppressed carcinoma cell growth by regulating cell cycle, we performed cell cycle analysis in S100A8/A9-expressing and non-expressing KB cells. Rapidly dividing cells such as carcinomas progress through cell cycle at higher rates than normal cells. Cellular changes in DNA content can be measured over time by propidium iodide (PI)-staining. To determine differences in cell cycle progression, carcinoma cells were synchronized at G1/S phase by serum starvation overnight followed by treatment with aphidicolin for 12 hours in normal growth medium. Following release from aphidicolin-induced G1/S blockage, KB wild-type, KB-EGFP and KB-S100A8/A9 cells progressed through G1/S phase and entered G2/M phase at approximately the same rate as determined by PI-staining of DNA (FIG. 9A, 9C). KB and KB-EGFP cells exited G2/M phase by 11 hours and the G2/M cell population returned to background levels by 13 hours postsynchrony. KB-S100A8/A9 cells, however, appeared to arrest in G2/M phase for at least three hours. Consistent with these observations, KB-S100A8/A9 cells showed fewer mitotic cells at nine hours post-synchrony and remained in metaphase longer than KB-EGFP cells (FIG. 9B, 9D).

S100A8/A9 Modulates G2/M Signaling Pathway

Figure 10:
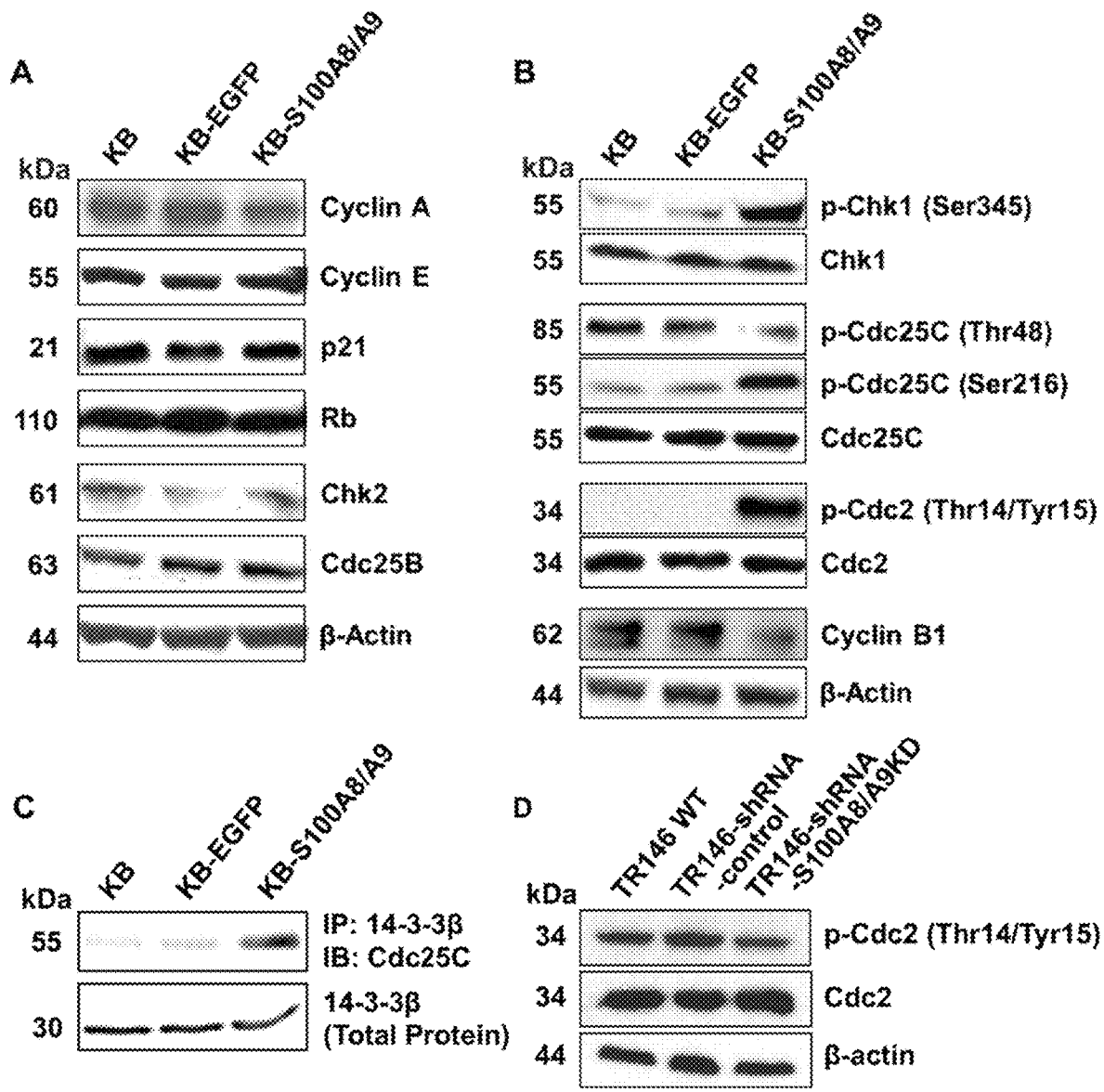
FIG. 10. S100A8/A9 modulates G2/M cell cycle checkpoint regulating molecules in SCC. Expression and phosphorylation (activation/inactivation) status of cell cycle regulators are shown by immunoblot analysis. Data shown are representative of multiple independent repeat experiments. Goat anti-β-actin polyclonal IgG was used to detect β-actin as protein loading control. (A) Expression of G1/S regulating proteins, cyclin A, cyclin E, p21 and Rb, Chk2 and Cdc25B, in KB, KB-EGFP and KB-S100A8/A9. Phosphorylation of p-Chk2 (Thr68) was not detectable in any cell, with or without S100A8/A9 expression (not shown). (B) Expression and phosphorylation status of G2/M regulators, Chk1/p-Chk1 (Ser345), mitotic active p-Cdc25C (Thr48), Cdc25C/p-Cdc25C (Ser216), Cdc2/p-Cdc2 (Thr14/Tyr15), and cyclin B1. (C) Immunoblotting (IB) of Cdc25C protein co-immunoprecipitated (IP) with 14-3-3β captured with rabbit anti-14-3-3β polyclonal IgG. Immunoblotting of total 14-3-3β protein is also shown. (D) Protein levels of S100A8, S100A9, Cdc2 and Cdc2-(Thr14/Tyr15) in wild-type TR146 (TR146 WT), control shRNA transfectant (TR146-shRNA-control) and shRNA-induced S100A8/A9 knockdown (TR146-shRNA-S100A8/A9KD) cells.

To confirm whether S100A8/A9 regulates the G2/M checkpoint, we tested protein expression and activation status of G1/S and G2/M cell cycle checkpoint regulators by immunoblotting. KB, KB-EGFP and KB-S100A8/A9 cells expressed similar levels of the cell cycle regulators cyclin A, cyclin E, p21, Rb, Chk2, and Cdc25B (FIG. 10A), suggesting that the G1/S checkpoint was unaffected by S100A8/A9 expression. Cyclin Bl, which is a G2/M checkpoint regulator required for cyclin-dependent kinase 1 (Cdc2) activities during entry into mitosis (Soni et al., 2008. *Cell Cycle* 7: 1285-1300), showed lower mRNA (data not shown) and protein (FIG. 10B) levels in KB-S100A8/A9 than KB and KB-EGFP cells. More significantly, S100A8/A9 expression increased phosphorylation of the G2/M-associated checkpoint kinase p-Chk1 (Ser345), phosphatase p-Cdc25C (Ser216) and p-Cdc2 (Thr14/Tyr15) in KB-S100A8/A9, but did not alter expression levels of these proteins (FIG. 10B). S100A8/A9 also decreased the mitotic active form of p-Cdc25C (Thr48) (FIG. 10B). In KB-S100A8/A9 cells, we found greater co-immunoprecipitation of Cdc25C with 14-3-3β (FIG. 10C), suggesting increased interaction between Cdc25C and 14-3-3β. Total 14-3-3β protein expression was unaffected by S100A8/A9 expression. Knockdown of S100A8/A9 in TR146-shRNA-S100A8/A9KD cells decreased p-Cdc2 (Thr14/Tyr15) phosphorylation (FIG. 10D). Taken together, our results suggest that S100A8/A9 modulates the canonical G2/M signaling pathway consistent with maintenance of a G2/M checkpoint delay.

S100A8/A9 Interacts with PP2A Phosphatase and Increases Activity

Figure 11:
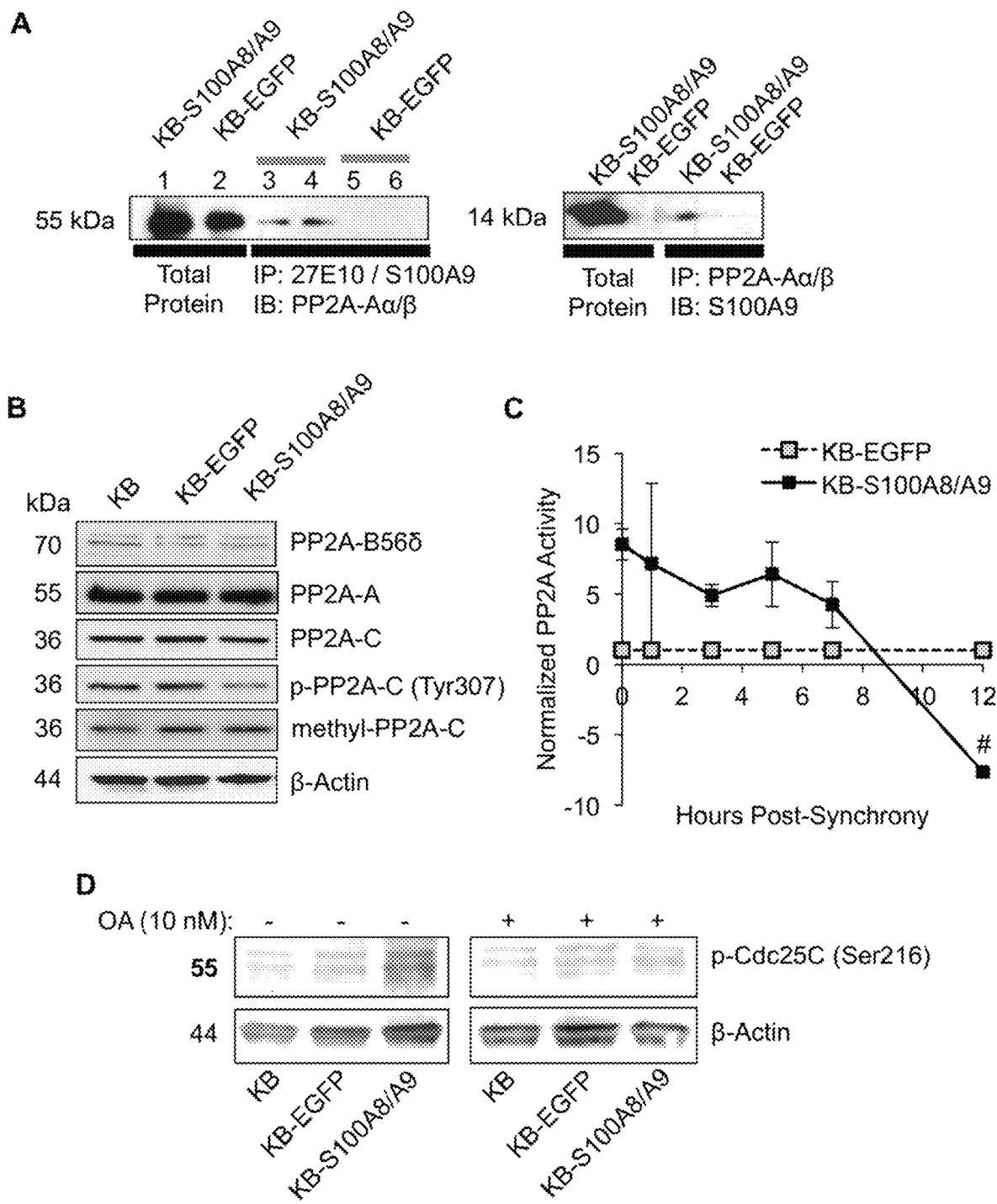
FIG. 11. S100A8/A9 interaction with PP2A phosphatase increases activity. (A) PP2AAα/β co-immunoprecipitated (IP) with either S100A8/A9 complex (IP with 27E10 antibody) or S100A9 subunit (left panel) and S100A9 (used as S100A8/A9 complex marker protein) co-IP with PP2A-Aα/β subunit as detected by immunoblotting (IB). (B) PP2A subunit protein expression, phosphorylation and methylation compared in KB, KB-EGFP and KB-S100A8/A9 cells as detected using IB. Blot shown is a representative of multiple repeats (n≥3) of total protein lysates separated in 10% SDS-PAGE gels. β-actin was used as protein loading control. (C) The PP2A-C phosphatase activities in KB-EGFP and KB-S100A8/A9 cells were normalized to the detectable PP2A-Aα/β co-immunoprecipitated with S100A8/A9 (27E10 antibody) shown in A, and then further normalized to KB-EGFP levels. Data was shown as Mean±SE (n=2). #Error bars not visible. (D) Inhibition of S100A8/A9-dependent p-Cdc25C (Ser216) phosphorylation by 10 nM okadaic acid (OA). Expression of p-Cdc25C in the absence (left panel) and presence of OA (right) as detected by IB.

To identify candidate cell cycle regulators that might directly interact with S100A8/A9, a curated database of known and predicted protein-protein interacting partners (Ingenuity Pathway Analysis, Genedata Inc., San Francisco, CA) was interrogated. We found that S100A8/A9 might be a binding partner and modulator of activity of protein phosphatase 2A (PP2A), a known cell cycle regulator. PP2A is a heterotrimeric holoenzyme with three subunits: structural protein subunit A, regulatory subunit B, and catalytic subunit C. PP2A-C catalytic activity is negatively regulated by phosphorylation at Tyr307 and C-terminal Leu309 methylation is essential for the overall phosphatase activity. The PP2A-B 566 isoform has been reported to control Cdc25C and G2/M cell cycle checkpoint activity (Guenin et al., 2008. *Int J Oncol* 32: 49-57; Perrotti et al., 2008. *Cancer Metastasis Rev* 27: 159-168). S100A8/A9 binding to PP2A was confirmed by co-immunoprecipitation assay using antibodies against S100A8/A9 complex or PP2A. PP2A co-immunoprecipitated with S100A8/A9 when captured with 27E10 antibody (specific for S100A8/A9 complex) (FIG. 11A). Interaction was also confirmed by detection of S100A9 (used as a marker for S100A8/A9 complex) when captured with PP2A-Aa/β antibody. S100A8/A9 expression in KB-S100A8/A9 cells did not affect PP2A subunit protein levels (subunits Aa/β, B566 and Ca/β) using immunoblotting analysis; phosphorylation of subunit Ca/β (Tyr307), however, appeared reduced (FIG. 11B). C-terminal methylation appeared unaffected by S100A8/A9 expression as identified by anti-methylated-PP2A-C (Leu309) antibody.

To determine PP2A phosphatase activity, an antibody against PP2A-C catalytic subunit was used to immunoprecipitate the holoenzyme from cell lysates with or without S100A8/A9 expression. The phosphatase activity of immunoprecipitated PP2A was then determined by measuring the level of inorganic phosphate (Pi) release from a phosphopeptide substrate. For up to seven hours post-synchrony, PP2A phosphatase activity was approximately five-fold greater in the presence of S100A8/A9 compared to the absence (KB-EGFP cells) of S100A8/A9, decreasing by seven-fold at 12 hours postsynchrony. Phosphatase activities were normalized to detectable PP2A-Aa/β levels co-immunoprecipitated with S100A8/A9 (27E10 antibody) (FIG. 11C). S100A8/A9-dependent modulation of PP2A activity in KB cells, therefore, appears to depend on the phases of the cell cycle. Similar changes in PP2A activities were also observed when cell lysate from KB-EGFP was preincubated with 1 μg of purified S100A8/A9 (data not shown). KB-S100A8/A9 cells treated with a PP2A inhibitor, okadaic acid (OA) showed similar levels of p-Cdc25C (Ser216) as KB and KB-EGFP cells, suggesting that S100A8/A9-mediated increase in p-Cdc25C (Ser216) phosphorylation was inhibited (FIG. 11D).

Thus, as members of the S100 family of proteins, S100A8 and S100A9 in complex (S100A8/A9, or calprotectin) are thought to have a regulatory role in cell cycle progression. In this study, we found that S100A8/A9 functions as a negative regulator of cell division and growth in KB cells and in TR146 human carcinoma cells by inducing G2/M cell cycle arrest. KB cells were used as an in vitro model for gain-of-function study since this carcinoma cell line lacks the expression of S100A8 and S100A9 at both mRNA and protein levels. TR146 is a more differentiated HNSCC cell line with detectable S100A8/A9 expression compared to other lines available. The ratios of S100A8 to S100A9 cannot be compared in TR146 and KB-S100A8/A9 cells, yet the attributed role in control of the G2/M checkpoint appears to be the same. Hence, if individual subunits are present in excess in either cell line, such discrepancies do not explain the purported intracellular function of S100A8/A9. From our current findings, reduced levels of S100A8/A9 and resulting loss of function could therefore de-regulate growth in SCCs and contribute to carcinogenesis. In inflammatory or hyperproliferative oral lesions and HNSCC tissues, S100A8/A9 complex is markedly down-regulated at both mRNA and protein levels compared to normal mucosa (S100A8/A9 is generally not detectable in squamous carcinoma cells). Moreover, we found that HNSCC show approximately 10-fold lower S100A8 and S100A9 gene expression than NAT. S100A8/A9 levels in NAT may reflect field cancerization. Although S100A8/A9 gene expression in mucosal tissues of cancer-free individuals may be even greater, decreased S100A8/A9 expression levels are clearly associated with carcinogenesis.

To determine whether the dysregulation of S100A8/A9 in HNSCC is a cause or an effect of the cancer phenotype, we sought to determine a role in cell cycle regulation. S100A8/A9 protein is found in the cytoplasm and appears to localize in the nucleus (The Human Protein Atlas database, accessible at www.proteinatlas.org) or perinuclear area (Champaiboon et al., 2009. *J Biol Chem* 284: 7078-7090) depending on cell growth status. During cell division and when controlling the G2/M checkpoint, S100A8/A9 localizes to the microtubule organizing centers at the poles of the mitotic spindles. The G2/M checkpoint is under the control of the checkpoint kinases Chk1/2 (Agarwal et al., 2003. *Oncogene* 22: 8271-8282; Taylor et al., 2001. *Oncogene* 20: 1803-1815). Chk1/2 inactivate protein phosphatase Cdc25, which is required for activation of cyclin B/cyclin-dependent kinase 1 (CDK1, also known as Cdc2) complex and entry into mitosis (Agarwal et al., 2003. *Oncogene* 22: 8271-8282; Taylor et al., 2001. *Oncogene* 20: 1803-1815). In the presence of S100A8/A9, we found that the level of activating phosphorylation of p-Chk1 (Ser345) was increased. Similarly, inhibitory phosphorylation of p-Cdc25C (Ser216) and p-Cdc2 (Thr14/Tyr15) was elevated. Ser345-hyperphosphorylation of the G2/M-specific kinase p-Chk1 suggests that p-Chk1 (Ser345) is likely activated (Shiromizu et al., 2006. *Genes Cells* 11: 477-485) by S100A8/A9 through a mechanism that is yet unknown. An attempt to determine protein-protein interaction between S100A8/A9 and Chk1 by co-immunoprecipitation was unsuccessful (data not shown). In the canonical G2/M checkpoint signaling pathway, activated p-Chk1 (Ser345) phosphorylates the G2/M-specific phosphatase Cdc25C at Ser216 and promotes its binding to the molecular chaperone 14-3-3β (Peng et al., 1997. *Science* 277: 1501-1505; Peng et al., 1998. *Cell Growth Differ* 9: 197-208) (see FIG. 12). Binding to 14-3-3β inactivates and promotes cytosolic accumulation of p-Cdc25C (Ser216) (Graves et al., 2001. *Oncogene* 20: 1839-1851). Alternatively, active p-Cdc25C (Thr48) dephosphorylates inhibitory residues Thr14 and Tyr15 of p-Cdc2 and activates the Cdc2/cyclin B1 complex, resulting in entry into mitosis (Ozen et al., 2005. *Clin Cancer Res* 11: 4701-4706). S100A8/A9 expression in KB-S100A8/A9 cells induced a marked increase in the levels of inhibitory p-Cdc25C (Ser216), Cdc25C/14-3-3β complex, and p-Cdc2 (Thr14/Tyr15). The level of mitotically active p-Cdc25C (Thr48) and cyclin B1 was greatly reduced in the presence of S100A8/A9. These results indicate an S100A8/A9-dependent activation of G2/M DNA damage checkpoint, leading to inactivation of the Cdc25C and mitotic arrest.

S100A8/A9-induced inactivation of Cdc25C and cyclin B1/Cdc2 complex to negatively regulate the G2/M cell cycle progression is suggested to reduce carcinoma growth and may inhibit tumor formation. Indeed, S100A8/A9-expressing KB-S100A8/A9 and TR146 cells both showed significant reduction in growth and clonogenicity when compared to S100A8/A9-negative or S100A8/A9-knockdown cells. Although KB-S100A8/A9 cells expressed less S100A8 and S100A9 than normal tissue as represented by the NAT (relative to GAPDH housekeeping gene as intracellular control), ectopic expression caused substantial growth suppression. Since knockdown of S100A8/A9 in TR146 cells resulted in marked increase in growth and colony formation in soft agar, our data, therefore, strongly suggests a concentration-dependent effect of S100A8/A9 on carcinoma cell growth and clonogenicity. Further loss of S100A8/A9 expression in tissues would be expected to accelerate tumor growth and malignant transformation in HNSCC.

Although the loss of both G1/S and G2/M checkpoints are required for increased growth and proliferation in carcinomas, S100A8/A9-dependent induction of G2/M checkpoint contributed significantly to the suppression of mitotic activity and growth of KB cells. Expression of S100A8/A9 caused KB-S100A8/A9 cells to arrest and accumulate at G2/M, inhibiting progression into mitosis without affecting the rate of G1/S-to-G2/M transition. Overall, this growth inhibiting effect of S100A8/A9 is consistent with a report in epidermal keratinocytes, where ectopic transient expression of S100A8/A9 suppressed cell division and proliferation (Voss et al., 2011. FEBS Lett 585: 440-446). In our experiments, the effect on carcinoma growth could not be attributed to extracellular S100A8/A9 protein since sequence analysis of S100A8 and S100A9 genes shows no upstream signal peptides, which are required for canonical secretion. Furthermore, in our hands, extracellular S100A8/A9 from TR146 or transfected KB was below detectable levels as determined using a specific ELISA (data not shown). Hence, S100A8/A9 as studied is a cytosolic protein complex and is unlikely to be secreted by epithelium into extracellular space under normal growth conditions. S100A8/A9 expression also had no apparent effect on the levels of G1/S-associated downstream regulator proteins and the percentages of S100A8/A9-positive and -negative cells in G1/S and S phase were similar following the release from synchrony. Although a defect in G1/S has not been rigorously excluded, S100A8/A9-mediated regulation of cell cycle is strongly suggested to affect G2/M.

We now report the first mechanistic insights to explain how S100A8/A9 signals inactivation of Cdc25C and induction of G2/M cell cycle arrest. Reduction of mitotic p-Cdc25C (Thr48) phosphoprotein is likely signaled through dephosphorylation by a Ser/Thr protein phosphatase 2A (PP2A). PP2A has been reported to induce cell cycle arrest by targeting and dephosphorylating p-Cdc25C (Thr48) (Forester et al., 2007. Proc Natl Acad Sci USA 104: 19867-19872; Margolis et al., 2006. Cell 127: 759-773; Guenin et al., 2008. Int J Oncol 32: 49-57), allowing Cdc25C to be phosphorylated at Ser216 by p-Chk1 (Ser345) for inactivation and nuclear export as described above.

The PP2A-Cα/β subunit is the enzymatic active site of PP2A and its phosphatase activity is controlled by phosphorylation at Tyr307 and methylation at Leu309, which is also essential for the holoenzyme assembly. In KB-S100A8/A9 cells, expression of S100A8/A9 did not affect the protein level of PP2A-Aα/β, PP2A-B56δ (a regulatory subunit known to signal targeting of Cdc25C) or PP2A-Cα/β subunits. Leu309 methylation levels of PP2A-C (methyl-PP2A-C) subunit were also similar in KB-S100A8/A9, KB-EGFP and wild-type control cells. These data suggest that S100A8/A9 has no regulatory effects on PP2A expression or the holoenzyme assembly in KB cells. The phosphorylation level of the Tyr307 inhibitory residue of PP2A-C, however, was reduced in KB-S100A8/A9 cells, suggesting increased phosphatase activity of the enzyme.

S100A8/A9 expression augmented pre-mitotic PP2A phosphatase activity in KB-S100A8/A9-transfected cells. When purified S100A8/A9 protein was preincubated with KB-EGFP cell lysate (lacking S100A8/A9), PP2A activity was modulated similarly. Hence, S100A8/A9 appears to directly signal an increase in dephosphorylation and activation of PP2A. Post-mitotic PP2A phosphatase activity was markedly suppressed by S100A8/A9 expression, suggesting biphasic, cell cycle-dependent regulation by S100A8/A9. PP2A phosphatase activity was markedly elevated at time=0 hour post-synchrony. The level at t=0 may reflect activity during G1/S. PP2A also plays a role in G1/S cell cycle arrest (Pitre et al., 2012. Mol Biol Cell 23: 1243-1253; Hofstetter et al., 2012. PLoS One 7: e30059), independent of the G2/M checkpoint signaling pathway. The increase in PP2A phosphatase activity observed at t=0 was likely due to the transient G1/S blockage by aphidicolin that was used to synchronize the cells at G1/S. Although S100A8/A9 did not alter G1 to S cell cycle progress, an S100A8/A9-independent inhibition of G1/S (pharmacologically by aphidicolin in this case) could have signaled PP2A activation. Most importantly, PP2A phosphatase activity at G1/S was either dependent on or enhanced by S100A8/A9 expression in KB-S100A8/A9 cells and will be further investigated in our future studies. Interestingly, PP2A and S100A8/A9 appeared to interact directly based on co-immunoprecipitation experiments, suggesting a possible mechanism of PP2A activation by the S100A8/A9 protein complex.

To provide further evidence that S100A8/A9-induced inactivation of Cdc25C was dependent on PP2A activity, okadaic acid treatment, which specifically inhibits PP2A activity, was shown to reduce p-Cdc25C (Ser216) phosphorylation in the presence of expressed S100A8/A9. This finding is consistent with the literature since inactivation of Cdc25C through Ser216 phosphorylation (by Chk1) requires dephosphorylation of Cdc25C at Thr48, a known substrate for PP2A (Zhou et al., 2000. Mol Cell 6: 873-883). Okadaic acid treatment, therefore, inhibited S100A8/A9-induced PP2Adependent phosphorylation of inhibitory p-Cdc25C (Ser216). Under normal growth conditions, therefore, S100A8/A9 mediates PP2A reactivation of the G2/M checkpoint and cell cycle delay.

S100A8/A9-dependent reduction in expression of cyclin B1 and hyperphosphorylation of p-Cdc2 (Thr14/Tyr15) shown in this study are also consistent with Cdc2 inactivation and G2/M checkpoint arrest as commonly reported in carcinomas (Yang et al., 2010. Free Radic Res 44: 792-802; Maalouf et al., 2009. Int J Radiat Oncol Biol Phys 74: 200-209; Wang et al., 2008. J Cell Biochem 104: 1181-1191). As observed in the knockdown of S100A8/A9 by shRNA in TR146 HNSCC cells, reduction in S100A8/A9 significantly increased growth and colony formation in soft agar in association with p-Cdc2 (Thr14/Tyr15) hypophosphorylation. Loss of S100A8/A9-dependent regulation of the G2/M checkpoint, increased signaling of the G2 to M transition, and the constitutive dysregulated G1/S checkpoint were strongly suggested to cause the increase in growth rate of the TR146 cells.

Figure 12:
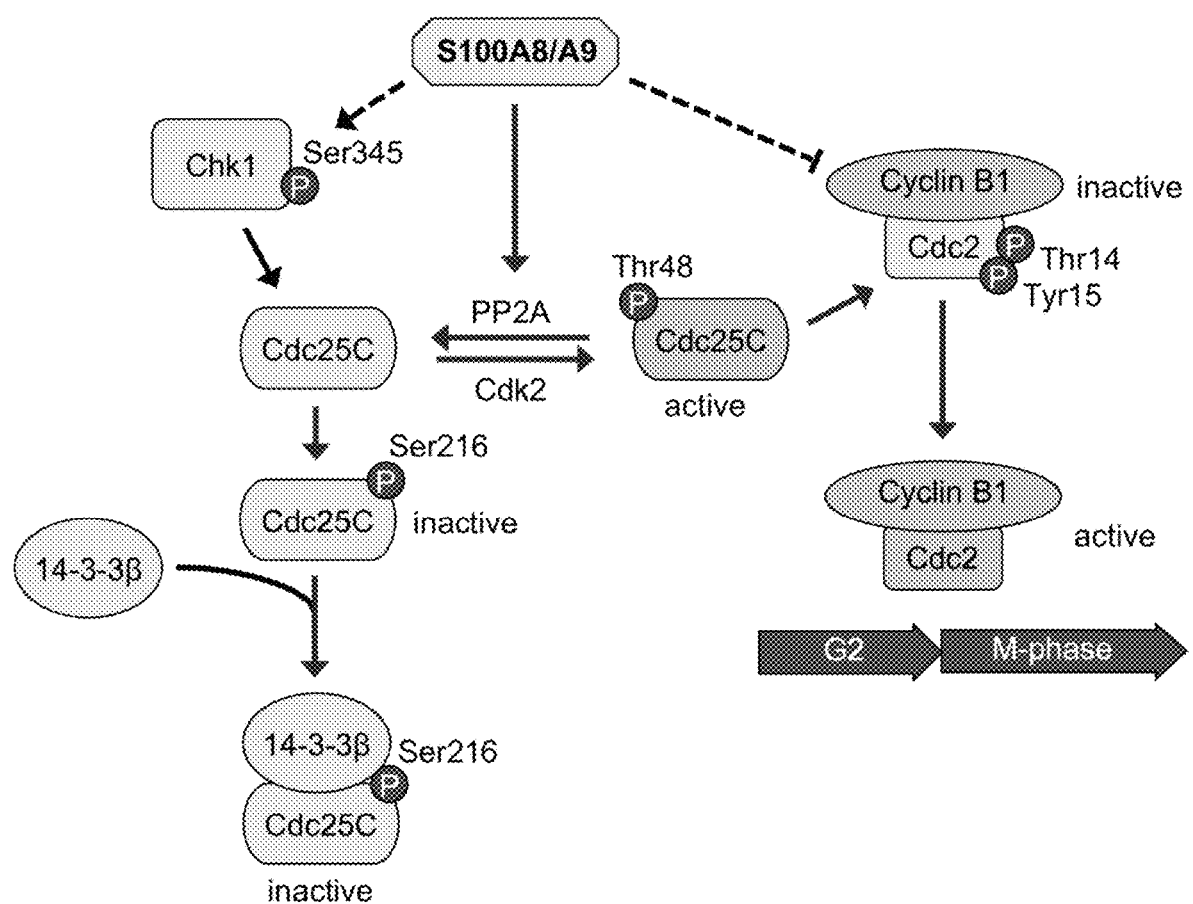
FIG. 12. Proposed S100A8/A9 (calprotectin)-mediated regulation of the G2/M cell cycle checkpoint signaling pathway as summarized in this report. Solid line represents direct regulation; dashed line represents unknown mechanism.

In summary, we propose a model that now includes S100A8/A9 as a key signaling mediator in the induction of G2/M cell cycle checkpoint and mitotic arrest through a PP2Adependent pathway (FIG. 12). S100A8/A9 expression increases PP2A phosphatase activity, potentially through direct protein-protein interaction and dephosphorylation of the inhibitory residue Tyr307 of the catalytic subunit PP2A-C, increasing activation of PP2A. Activated PP2A is hypothesized to target and dephosphorylate p-Cdc25C (Thr48), allowing Cdc25C to be phosphorylated by Chk1 at inhibitory residue Ser216 (Perry et al., 2007. Cell division 2: 12). In carcinoma cells the G2/M cell cycle checkpoint is dysregulated, resulting in increased phosphorylation of Thr48 of p-Cdc25C and accelerated cell growth. S100A8/A9 activates the G2/M checkpoint through PP2A to induce mitotic arrest (and reduction in growth) by reducing the level of p-Cdc25C (Thr48) and by increasing the levels of p-Chk1 (Ser345) and p-Cdc25C (Ser216). Whether activation of Chk1 kinase (by phosphorylation at Ser345) and G2/M checkpoint is directly signaled by S100A8/A9 expression or by PP2A dephosphorylation of Cdc25C at Thr48 is still unclear, but both Thr48 and Ser216 residues of Cdc25C cannot be phosphorylated at the same time. Phosphorylated p-Cdc25C (Ser216) is targeted and bound by 14-3-3β, leading to inactivation and cytosolic accumulation of Cdc25C. As a result, cyclin Bl/p-Cdc2 (Thr14/Tyr15) complex is inactivated, arresting cell cycle at the G2/M checkpoint. Other mitotic checkpoint inhibitors are unaffected. S100A8/A9 (or calprotectin) may therefore function as a tumor suppressor in squamous epithelial cells and reduced expression may serve as an indicator for disease progression. Thus, artificially increasing intracellular expression of S100A8/A9 in HNSCC and other SCCs may prove to be an effective therapeutic strategy.

For example, intracellular S100A8/A9 reduces floor-of-mouth tumor (orthotopic) formation in mice. Tumor cells suspended in MATRIGEL (BD Biosciences, San Jose, CA) were inoculated into the floor of the mouth of nu/nu mice using an established protocol (Henson B. et al., 2007. *J Oral Pathol Med.* 36:363-370). KB cells expressing S100A8/A9 produce 65% smaller (p<0.02) orthotopic tumors by day 17 than control sham transfected KB cells (expressing EGFP) (FIG. 13A). S100A8/A9 expression correlated with more discrete and less invasive tumors (FIG. 13B), decreased necrotic areas, and a less aggressive histological phenotype (FIG. 13C). Conversely, TR146 buccal carcinoma cells formed floor-of-the-mount (orthotopic) tumors that were 20% larger than tumors formed after sham knockdown in TR146 cells (FIG. 14). These data indicate that expression of S100A8/A9 in tumor cells reduce the volume and apparent invasiveness of tumors forming at the floor-of-the-mouth.

Thus, we have shown that expression of S100A8/A9 by carcinoma cells in floor-of-the-mouth tumors (orthotopic) is inversely related to the size of the tumors that form. Hence, S100A8/A9 can function as a tumor suppressor. Methods that result in increased expression of S100A8/A9 can be used as therapeutic methods for certain cancers that involve neoplasias of epithelial cells such as, for example, head and neck cancers, including but not limited to tumors of the floor-of-the-mouth. Such methods can include introducing into a cell one or more mRNA polynucleotides that encode components S100A8/A9 so that the cell increases production of S100A8/A9. In alternative embodiments, the method can include administering to the subject one or active agents that result in an increase in expression of S100A8/A9. Exemplary active agents include, for example, regulatory cytokines such as IL-1α, IL-1α with keratinocyte growth factor, IL-6, IL-8 with and without CXCL8, IL-22, TNFα, CXCL1, CXCL2, CXCL3, CCL20. Exemplary active agents also include compounds that upregulate S100A8/A9 such as, for example, phorbol myristate acetate.

In one aspect, therefore, this disclosure describes a method for decreasing the likelihood and/or severity of infection of mucosal epithelia by a pathogenic microbe. The method generally involves introducing into a cell an mRNA encoding a polypeptide involved in innate immunity and permitting the cell to express the polypeptide in an amount effective to decrease the likelihood that the cell is infected by a pathogen. In another aspect, this disclosure describes a method of decreasing the likelihood or extent of epithelial cell proliferation. The method generally involves introducing into an epithelial cell an mRNA encoding a polypeptide involved in suppressing cell proliferation and permitting the cell to express the polypeptide in an amount effective to decrease the likelihood that the cell proliferates in an anchorage-independent environment. As used herein, the term "polypeptide" refers to a sequence of amino acid residues without regard to the length of the sequence. Therefore, the term "polypeptide" refers to any amino acid sequence having at least two amino acids and includes full-length proteins.

In various embodiments, the method may be performed in vitro or in vivo. The mRNA may be introduced into the cell by any suitable method. When introducing the mRNA in vivo, one typically can introduce the mRNA into the cell with the aid of an in vivo delivery vehicle. Exemplary in vivo delivery vehicles can include components such as, for example, TransIT-mRNA and TransIT-mRNA boost reagents (Mirus Bio LLC, Madison WI).

In some embodiments, the cell may be, or be derived from, an epithelial cell such as, for example, a cell of the mucosal epithelium. Thus, for in vivo embodiments of the method, exemplary cells include carcinoma cells. Exemplary cells further include cells of the oral mucosa, vaginal mucosa, genital mucosa, tonsil epithelium, oropharynx, nasopharynx, lungs, gastrointestinal mucosa, or mucosal epithelium surrounding the eye. Consequently, the methods may be used as therapy for conditions that include, for example, carcinoma, gingivitis, periodontitis, oral candidiasis, streptococcal sore throat, mucositis, bacterial bronchitis, bacterial pneumonia, vaginosis, other vaginal and cervicovaginal infections, vaginal yeast infections, gastrointestinal infections (e.g., *Listeria* and *Salmonella* GI infections), infections of the eye, mucosa and/or perimucosal infections. The methods are equally amenable to introducing mRNA to mucosal and related epithelia to express transiently virtually any protein that may be of preventive or therapeutic value such as tumor suppressors or proteins to improve wound healing. For example, proteins that might improve healing of recalcitrant skin wounds, antagonize skin cancers such as basal cell carcinoma, squamous cell carcinoma and melanoma, prevent scarification and keloid formation, or reverse the angiogenic process in epidermal nevi could be expressed using mRNA transfections.

For in vitro embodiments of the method, the cells can be, or be derived from any of the in vivo cell types identified immediately above. Alternatively, the cells can be, or be derived from, any suitable epithelial cell line such as, for example, human KB cells (ATCC CCL-17).

The mRNA encodes a polypeptide involved in innate immunity. Exemplary polypeptides involved in innate immunity include, for example, cathelicin antimicrobial protein (CAMP), calprotectin, S100A8, S100A9, any α-defensin, β-defensin, S100A7, S100A12, secretory leukocyte inhibitor, lipocalin 2, and lysozyme. The mRNA also can encode any combination of two or more polypeptides involved in innate immunity. As used herein, "a polypeptide involved in innate immunity" refers to a full-length polypeptide, an effective fragment thereof, or a precursor of a full-length polypeptide or effective fragment. For example, a CAMP mRNA may encode CAP-18, a precursor that is activated to LL-37 by proteinase 3, a serine protease. Beyond innate immunity, mRNA cargoes can encode virtually any host polypeptide to introduce, replace, or augment any function.

The method can be used to decrease the likelihood and/or extent of infection by a pathogen. The pathogen may be any pathogen for which the cell is a target of infection. Exemplary pathogens include, for example, fungi such as, for example, *Candida albicans*, *Acinetobacter baumannii*,

*Aspergillus* spp. (e.g., *A. nidulans* and *A. fumigatus*), and bacteria such as, for example, *Capnocytophaga sputigena, Escherichia coli, Staphylococcus* spp. (e.g., *S. aureus* and *S. epidermis*), *Streptococcus* spp. (e.g., *S. pneumonia, Streptococcus* group A, *Streptococcus* group B, and *Streptococcus* group C), *Listeria monocytogenes, Salmonella typhimurium, Borrelia burgdorferi, Porphyromonas gingivalis, Tannerella forsythia, Treponema denticola, Pseudomonas aeruginosa, Chlamydia* spp., *Neisseria* spp., *Gardnerella* spp., and *Trichomonas* spp.

In some embodiments, the mRNA can include a stabilizing moiety that increases the half-life of the mRNA once the mRNA is introduced into the cell. The stabilizing moiety can include a 5' cap such as, for example, anti-reverse cap analogue (ARCA) or a 7-methylguanylate ($m^7G$) cap. In some embodiments, the stabilizing moiety can include a 3' poly(A) extension. Exemplary poly(A) extensions can include any number of adenine residues. In certain embodiments, a poly(A) extension can include 64 adenine residues or 150 adenine residues with little apparent difference in the half-life of the mRNAs. Stabilization can also involve using modified bases when synthesizing the mRNA constructs.

In some embodiments, the method can further include permitting the pathogen to contact the cell into which the mRNA has been introduced.

For in vivo methods, the cell to which the mRNA is introduced may be a cell of a subject having or at risk of having a condition caused by infection by the pathogen. As used herein, a subject having a condition caused by infection by the pathogen refers to a subject exhibiting one or more symptoms or clinical signs of the condition. "Symptom" refers to any subjective evidence of disease or of a patient's condition. "Sign" or "clinical sign" refers to an objective physical finding relating to a particular condition capable of being found by one other than the patient. As used herein, the term "at risk" refers to a subject that may or may not actually possess the described risk. Thus, for example, a subject "at risk" of infectious condition is a subject present in an area where other individuals have been identified as having the infectious condition and/or is likely to be exposed to the infectious agent even if the subject has not yet manifested any detectable indication of infection by the microbe and regardless of whether the animal may harbor a subclinical amount of the microbe.

Accordingly, introduction of the mRNA can be performed before, during, or after the subject first exhibits a symptom or clinical sign of the condition or, in the case of infectious conditions, before, during, or after the subject first comes in contact with the infectious agent. Treatment initiated after the subject first exhibits a symptom or clinical sign associated with the condition—i.e., therapeutic treatment—may result in decreasing the severity of symptoms and/or clinical signs of the condition, completely resolving the condition, and/or decreasing the likelihood of experiencing clinical evidence of the condition compared to an animal to which the composition is not administered. Similarly, treatment initiated before the subject first exhibits a symptom or clinical sign associated with the condition—i.e., prophylactic treatment—may result in decreasing the decreasing the severity of symptoms and/or clinical signs of the condition, completely resolving the condition, and/or decreasing the likelihood of experiencing clinical evidence of the condition compared to an animal to which the composition is not administered.

The method includes administering an effective amount of the composition to a subject having, or at risk of having, a particular condition. In this aspect of the invention, an "effective amount" is an amount effective to reduce, limit progression, ameliorate, or resolve, to any extent, the symptoms or clinical signs related to the condition.

A formulation containing the mRNA may be provided in any suitable form including but not limited to a solution, a suspension, an emulsion, a spray, an aerosol, or any form of mixture. The composition may be delivered in formulation with any pharmaceutically acceptable excipient, carrier, or vehicle. The formulation may further include one or more additives including such as, for example, an adjuvant or an inert carrier (e.g., a nanoparticle).

The amount of mRNA administered to a subject can vary depending on various factors including, but not limited to, the weight, physical condition, and/or age of the subject, the route of administration, the specific mRNA cargo, and/or the stability of the resulting protein expression. Thus, the absolute amount of mRNA included in a given unit dosage form can vary widely, and depends upon factors such as the mRNA cargo, the therapeutic indication, the species, age, weight and/or physical condition of the subject, as well as the method of administration. Accordingly, it is not practical to set forth generally the amount that constitutes an amount of mRNA effective for all possible applications. Those of ordinary skill in the art, however, can readily determine the appropriate amount with due consideration of such factors.

In some embodiments, mRNA may be administered, for example, in a single dose to multiple doses. Because the mRNA does not integrate into the genome of the subject, the therapeutic and/or prophylactic effect of introducing the mRNA into cells of the subject will naturally dissipate over time. Thus, a therapeutic or prophylactic regimen that involves introducing mRNA into a cell of a subject can include multiple treatments.

In another aspect, this disclosure describes a composition that includes an mRNA that encodes a polypeptide involved in innate immunity, as described herein, and an in vivo delivery vehicle. The composition can have anti-tumor, antimicrobial, and/or antifungal activity and may, therefore, be an anti-tumor, antimicrobial, and/or antifungal agent.

The mRNA described herein may be formulated in a composition along with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with mRNA without causing any undesirable biological effects or interacting in a deleterious manner with any of the other components of the pharmaceutical composition in which it is contained.

The mRNA may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, etc.), or topical (e.g., intranasal, intrapulmonary, intramammary, intravaginal, intrauterine, intradermal, transcutaneous, rectally, etc.). It is foreseen that a composition can be administered to a mucosal surface, such as by administration to, for example, the vaginal, nasal, or respiratory mucosa (e.g., by spray or aerosol). A composition also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing a vector containing the mRNA into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Culture

Human KB cells (American Type Culture Collection, ATCC CCL-17) were cultured in Modified Eagle's Medium (MEM, Mediatech Inc, Herndon, VA) supplemented with 10% Fetal Bovine Serum (FBS) at 37° C. in a 5% $CO_2$ incubator.

Bacteria

*L. monocytogenes* ATCC 104035 and *S. enterica* serovar Typhimurium (*S. typhimurium*) ATCC 14028 were grown in brain heart infusion medium (DIFCO, BD Diagnostic Systems, Sparks, MD) and on tryptic soy agar (DIFCO, BD Diagnostic Systems, Sparks, MD) at 37° C. *Listeria* and *Salmonella* cells were harvested from log phase and stationary phases, respectively, at an absorbance of 0.4-0.6 at 620 nm), and used to infect KB cells.

Plasmid Construction pGEM4Z.sslbbz.2bgUTR.150A (provided by Prof. Carl H. June & Dr. Yangbing Zhao, University of Pennsylvania) were digested using NotI and HindIII to remove the insertion (Zhao et al., 2010. *Cancer Res.* 70: 9053-9061.). Then open reading frames (ORFs) of EGFP (Primer pairs P1 & P2), human CAMP (Primer pairs P3 & P4), S100A8 (Primer pairs P5 & P6) and S100A9 (Primer pairs P7 & P8) containing Kozak sequence, were cloned into pGEM4Z.2bgUTR.150A (Table 1). On the other hand, S100A8 ORFs containing Kozak sequences were cloned into the first multiple cloning site (MCS) of pIRES vector (Clontech Laboratories, Inc., Mountain View, CA) via Nhe I and XhoI (Primer pairs P11 & P12). S100A9 ORFs containing Kozak sequence was cloned into the second MCS via XbaI and NotI (Primer pairs P13 & P14) (Table 1). Then A8-IRES-A9 fragments were amplified (Primer pairs P9 & P10) and also cloned into pGEM4Z. 2bgUTR.150A to generate plasmid pGEM4Z.A8-IRES-A9.2bgUTR.150A (Table 1).

TABLE 1

Oligonucleotides Probes

| Name | Fragments | Oligonucleotide sequence (5'-3') | SEQ ID NO: |
|---|---|---|---|
| Primers for fragments cloned into pGEM4Z. 2bgUTR. 150A vector | | | 1 |
| P1 (sense) | EGFP | *CCTAAGCTTGCCACC*ATGGTGAGCAAGGG | 2 |
| P2 (antisense) | | *ATTTGCGGCCGC*TTACTTGTACAGCTCGTCCATGCCGAG | 3 |
| P3 (sense) | CAMP | CCTAAGCTTGCCACCATGAAGACCCAAAGGGATGGCC | 4 |
| P4 (antisense) | | *ATTTGCGGCCGC*CTAGGACTCTGTCCTGGGTACAAGATTCC | 5 |
| P5 (sense) | S100A8 | *CCTAAGCTTGCCACC*ATGTTGACCGAGCTGGAGAAAGCC | 6 |
| P6 (antisense) | | *ATTTGCGGCCGC*CTACTCTTTGTGGCTTTCTTCATGGC | 7 |
| P7 (sense) | S100A9 | *CCTAAGCTTGCCACC*ATGACTTGCAAAATGTCGCAGCTG | 8 |
| P8 (antisense) | | ATTTGCGGCCGCTTAGGGGGTGCCCTCCCC | 9 |
| P9 (sense) | A8-IRES-A9 | *CCTAAGCTTGCCACC*ATGTTGACCGAGCTGGAGAAAGCC | 10 |
| P10 (antisense) | | ATTTGCGGCCGCTTAGGGGGTGCCCTCCCC | 11 |
| Primers for fragments cloned into pIRES vector | | | 12 |
| P11 (sense) | S100A8 | *CTAGCTAGCGCCACC*ATGTTGACCGAGCTGGAGAAAGC | 13 |
| P12 (antisense) | | *CCGCTCGAG*CTACTCTTTGTGGCTTTCTTCATGGC | 14 |
| P13 (sense) | S100A9 | GCTCTAGAGCCACCATGACTTGCAAAATGTCGCAGCTG | 15 |
| P14 (antisense) | | *ATTTGCGGCCGC*TTAGGGGGTGCCCTCCCC | 16 |

*a*Regions of oligonucleotide not derived from the genes/fragments are bold and italic.

IRES in the pIRES vector is a partially disabled sequence (Rees et al., 1996. *Biotechniques* 20: 102-110; Bochkov et al., 2006. *Biotechniques* 41: 283-284, 286, 288 passim). To construct native IRES (nIRES) between two MCS, pGEM4Z.A8-IRES-A9.2bgUTR.150A vectors were used as templates and amplified with the primer pair 5'-AAACGTCTAGGCCCCCCGAACC-3' (SEQ ID NO:17)/5'-TTTAACCTCGACTAAACA-CATGTAAAGCATGTGC-3' (SEQ ID NO:18). The products were purified and self-ligated to generate plasmids pGEM4Z.A8-IRES/mut1-A9.2bgUTR.150A. The primer pair 5'-ACCATGACTTGCAAAATGTCGCAGCTG-3' (SEQ ID NO:19)/5'-ATTATCATCGTGTTTTT-CAAAGGAAAACCAC-3'(SEQ ID NO:20) were used to amplify using pGEM4Z.S100A8-IRES/mut1-S100A9.2bgUTR as templates, then fragments were purified and self-ligated to generate plasmids pGEM4Z.A8-nIRES-A9.2bgUTR.150A.

In Vitro Transcription

Templates were amplified from corresponding plasmid constructs and extracted from gels. Purified fragments were treated with 0.5% SDS and 100 µg/ml Protease K at 50° C. for 30 minutes and extracted with phenol:chloroform:isoamyl alcohol (25:24:1) and then with chloroform. After ethanol precipitation, templates were dissolved in 10 mM Tris-HCl and stored at −80° C. Using mMESSAGE mMACHINE T7 Ultra Kit (Life Technologies Corp., Carlsbad, CA) or ScriptCap™ m7G Capping System/ScriptCap™ 2'-O-Methyltransferase kit (Cell Script, Madison, WI), mRNAs were synthesized and then purified using a MEGAclear Kit (Life Technologies Corp., Carlsbad, CA) followed by ethanol precipitation.

mRNA Transfections

At approximately 60%-90% confluence, cells were transfected with mRNAs using the TransIT-mRNA Kit Reagent (Minis Biol LLC, Madison, WI) according to the manufacturer's instructions.

Western Blot Analysis

Cells were extracted using Mammalian Cell-PE LB™ buffer (G-Biosciences, St. Louis, MO). The extracted proteins were separated by SDS-PAGE, transferred onto nitrocellulose membranes, and incubated with one of the following: rabbit anti-β-actin (DB070, Delta Biolabs, LLC, Gilory, CA), mouse anti-LL37 (sc-166770, Santa Cruz Biotechnolology, Inc., Santa Cruz, CA), mouse anti-S100A8 (sc-48352, Santa Cruz Biotechnolology, Inc., Santa Cruz, CA), rabbit anti-S100A9 (sc-20173, Santa Cruz Biotechnolology, Inc., Santa Cruz, CA), rabbit anti-PARP (#9542S, Cell signaling). Rabbit primary antibodies were then incubated with horseradish peroxidase (HP)-conjugated goat anti-rabbit antibodies, whereas mouse primary antibodies were incubated with HP-conjugated goat anti-mouse antibodies (secondary antibodies, Santa Cruz Biotechnology, Inc., Santa Cruz, CA). Immunoreactions were visualized using SuperSignal West Pico Chemiluminescent substrate (Thermo Fisher Scientific, Inc., Waltham, MA) and exposed to Amersham Hyperfilm ECL film (GE Healthcare Biosciences, Piscataway, NJ). Protein bands were quantified by Quantity One analysis (BioRad Laboratories, Inc., Hercules, CA).

Bacterial Invasion Assay

Bacterial invasion was determined by the antibiotic protection assay (Champaiboon et al., 2009. *J. Biol. Chem.* 284:7078-90; Nisapakultorn et al., 2001. *Infect. Immun.* 69: 3692-3696). Briefly, KB cells (1.0-1.2×10⁵ cells) were seeded overnight in 24-well plates. Cells were then incubated with *L. monocytogenes* ATCC 10403 S or *S. typhimurium* ATCC 14028 at a multiplicity of infection (MOI) of 100:1 and 1:1, respectively. After two hours of incubation, the monolayers were washed with DPBS (Sigma-Aldrich, St. Louis, MO), incubated for 1.5 hours in MEM supplemented with 10% FBS containing 100 µg/ml gentamicin (Sigma-Aldrich, St. Louis, MO), and cells were lysed by incubation with sterile distilled water for 15 minutes. Released bacteria were diluted, plated with a spiral plater (Spiral Biotech, Bethesda, MD), incubated overnight at 37° C., and then number of colony-forming units (CFUs) of intracellular bacteria was enumerated on a colony counter (C-110, New Brunswick Scientific, Enfield, CT).

In Vitro Toxicology Assay

The toxic effects of mRNA delivery in vitro were analyzed by quantitatively determining cell viability using 3-(4,5-Dimethylthiazol-2-yl)-2,5-diphenyltetrazolium bromide (MTT) assay (in vitro toxicology assay kit, Sigma-Aldrich, St. Louis, MO). Briefly, MTT solution (5 mg/ml) was added to each well in an amount equal to 10% of the culture medium volume. Cells were then incubated for two hours at 37° C., absorbance was measured at a wavelength of 570 nm, and the percentage of viable cells was calculated as the ratio of absorbances of transfected and untransfected cells.

Analysis of Apoptosis

To evaluate cell apoptotic status, transfected cells were evaluated for PARP cleavage using rabbit anti-PARP in Western blots as described above and by flow cytometry using the Annexin V-FITC Apoptosis Detection Kit (MBL International Corp, Watertown, MA) according to the manufacturer's recommendations. At times up to 72 hours following transfection, cells were trypsinized, washed with 2.5% FBS in PBS, and incubated with Annexin V-FITC plus propidium iodide in binding buffer at room temperature for 5 min in the dark. Stained cells were analyzed using a Becton Dickinson FACSCalibur flow cytometer (BD Biosciences, San Jose, CA) with CellQuest software, placing the FITC signal in FL1 and the propidium iodide signal in FL2. Cells that were positively stained by annexin-V-FITC were considered apoptotic (Pelicano et al., 2003. *J. Biol. Chem.* 278: 37832-37839).

Statistical Analysis

For each condition, at least three to six independent experiments were performed and analyzed. To analyze differences in mean values, the Student's t-test was applied using Excel software (Microsoft, Redmond, WA).

Quantitative Real-Time Polymerase Chain Reaction Analysis

Using Trizol reagent (Life Technologies Corp., Carlsbad, CA) and RNeasy plus Mini-kits (Qiagen, Valencia, CA), total RNA was isolated and reverse transcribed with Superscript III (Life Technologies Corp., Carlsbad, CA). Quantitative Real-time Polymerase Chain Reaction (qRT-PCR) was performed using PrimeTime pre-designed qRT-PCR assays (Hs.PT.42.1073747 for human CAMP, Hs.PT.42.3682141 for human S100A8, Hs.PT.42.3080635 for human S100A9, Hs.PT.45.227970.g for human ACTB; Integrated Device Technology, San Jose, CA). The expression level of CAMP, S100A8, S100A9 A8-IRES-A9 and A8-nIRES-A9 mRNA was normalized to ACTB mRNA.

Immunofluorescence

After CAMP, S100A8/S100A9 mRNA transfection for 16 hours, cells were fixed with 4% paraformaldehyde for 10 minutes, washed with PBS (pH 7.4), and then permeabilized with 0.25% Triton X-100 for 10 minutes. After blocking one hour with 1% BSA in PBS/0.1% Tween 20 and rinsing 3× with PBS, cells were incubated with mouse anti-calprotectin (mAb 27E10, sc-33714, Santa Cruz Biotechnology, Inc., Santa Cruz, CA) or mouse anti-LL37 (sc-166770, Santa Cruz Biotechnology, Inc., Santa Cruz, CA) for one hour, followed by Alexa Fluor 568-conjugated goat anti-mouse IgG or Alexa Fluor 488-conjugated goat anti-rabbit IgG (Life Technologies Corp., Carlsbad, CA) for one hour. For EGFP mRNA transfection, no antibody incubation was needed. Nuclei were stained with DAPI. Fluorescence images were captured using an epifluorescence microscope system. A8-IRES-A9 and A8-nIRES-A9 mRNA transfection for 40 hours were also performed.

Example 2

Cell Lines and Culture Conditions

The human carcinoma cell line KB (ATCC CCL-17), negative for S100A8/A9 expression, was cultured in Minimum Essential Medium (MEM). The human HNSCC cell line TR146 expressing S100A8/A9 endogenously was cultured in Dulbecco's Modified Eagle's Medium/Ham's F-12 (DMEM/F-12). TR146 cells were originally derived from a cervical lymph node metastasis of a well-differentiated buccal carcinoma (Rupniak et al., 1985. *J Natl Cancer Inst* 75: 621-635) and was a gift from Dr. Reuben Lotan, University of Texas, M.D. Anderson Cancer Center, Houston, TX (Eicher et al., 1996. *Clin Cancer Res* 2: 1659-1664). Both MEM and DMEM/F-12 culture media were supplemented with 10% heat inactivated fetal bovine serum (complete medium) and the cells were maintained in 5% CO2 at 37° C. Each cell line tested *Mycoplasma* negative by qPCR before use.

Stable Expression of S100A8/A9 in Human Carcinoma Cell Line

Carcinoma cells stably transfected to express S100A8/A9 (KB-S100A8/A9, formerly known as KB-MRP8/14) or sham control vector (KB-EGFP) were generated from KB cells as previously reported (Nisapakultorn et al., 2001. *Infect Immun* 69: 4242-4247). Briefly, KB cells were co-transfected with the mammalian expression vector, pIRES-EGFP (Clontech, Palo Alto, CA), containing S100A8 (MRP8) or S100A9 (MRP14) subunit genes, and the selectable marker pSV2-neo (G418 sulfate-resistant marker gene). The resulting cell line, KBS100A8/A9, expresses S100A8/A9 protein complex. The KB-EGFP sham-transfection control was generated by co-transfection of insertless pIRES-EGFP and pSV2-neo. Both KBS100A8/A9 and KB-EGFP were maintained in 700 µg/ml G418 sulfate (GENETICIN, Mediatech Inc., Manassas, VA). Cytosolic S100A8/A9 expression in transfected cells was verified both by sandwich enzyme-linked immunosorbent assay (ELISA) and indirect immunofluorescence with anti-S100A8/A9 heterodimer-specific monoclonal antibody, 27E10 (Bachem, King of Prussia, PA). Co-immunoprecipitation was also performed to confirm protein complex formation.

Gene Expression Analysis by Real-Time Quantitative RT-PCR

S100A8 and S100A9 expression was analyzed in clinical specimens of human head and neck squamous cell carcinoma (HNSCC) and matching NAT resected from three patients with stage II (T2N0M0), III (T3N0M0) and IVA (T4N0M0) tumors originating in the tongue, larynx and salivary gland, respectively. HNSCC tumor tissues from the three HNSCC patients and NAT, which showed no evidence of tumor cells, were obtained with informed consent through a commercial tissue bank (ProteoGenex, Inc., Culver City, CA). Tumors and NATs were snap frozen within 30 minutes post-resection, sectioned and analyzed for neoplastic cells. RNA was extracted from regions of the HNSCC specimens containing at least 70% tumor cells and NATs using Trizol and analyzed using an Agilent Bioanalyzer 2100 for quality control. Tumor and NAT total RNA from each patient was pooled separately, reverse transcribed, and quantified using real-time quantitative reverse-transcription polymerase chain reaction (qRT-PCR) with SYBR Green.

In separate experiments, total RNA was extracted from KB and TR146 cells using a Qiagen RNeasy Mini Kit, quantified using a NanoDrop spectrophotomer, and S100A8 and S100A9-specific mRNAs were quantified using real-time qRT-PCR as above.

Stable Knockdown of S100A8/A9 in a Human HNSCC Cell Line

To generate S100A8/A9-knockdown clones (TR146-shRNA-S100A8/A9KD) as previously described (Sorenson et al., 2012. *Mucosal Immunol.* 5: 66-75), TR146 cells (with endogenous S100A8/A9 expression) were transfected with the GeneEraser short hairpin RNA (shRNA) mammalian expression vector (Stratagene, Cedar Creek, TX) pGE-1 containing oligo sequences to produce interfering shRNA for S100A8 and S100A9 gene transcripts. Some cells were transfected with pGE-1 control vector, containing scrambled shRNA, to produce a negative control for S100A8 and S100A9 gene silenced clones (TR146-shRNA-control). Clones that grew in the presence of 250 µg/ml G418 sulfate were selected. S100A8/A9 gene and protein expression was quantified by qRT-PCR and immunoblot.

Growth of S100A8/A9-Positive and -Negative Cells

To determine anchorage-dependent growth rates, tumor cells were cultured on non-pyrogenic polystyrene tissue culture flasks in complete medium (see above), harvested by trypsinization and counted by trypan blue exclusion. Counts were confirmed using a Vi-Cell cell viability analyzer (Beckman Coulter, Fullerton, CA). Anchorage-independent growth was determined by enumerating cell colonies after growth in standard soft agar medium (0.25% agar in complete medium plated on top of 0.5% solid agar) for up to 2.5 weeks in 5% CO2 at 37° C.

Cell Synchronization and Cell Cycle Analysis

KB, KB-EGFP and KB-S100A8/A9 cells were seeded at a density of $1 \times 10^5$ cells/ml and cultured in complete medium as described earlier. To synchronize at G1/S, cells at 70% confluency (cultured for ~48 hours) were serum starved overnight and then blocked with 3 µg/ml aphidicolin in complete medium for 12 hours. To release the G1/S block and facilitate re-entry into the cell cycle, synchronized cells were washed three times with Dulbecco's phosphate-buffered saline (DPBS) without calcium and magnesium to remove aphidicolin and cultured in fresh medium containing 10% FBS. After release from G1/S block, cells were harvested at various time points, fixed in 70% ice-cold ethanol and DNA stained at 37° C. for 30 minutes with 25 µg/ml propidium iodide (PI) solution (containing 1 mg/ml RNase and 0.1% Triton X-100 in DPBS). PI-stained DNA content was analyzed using flow cytometry. Mitotic cells in synchronized cultures were also enumerated by immunostaining using phospho-histone H3 (Ser10)-specific polyclonal antibody, which was detected by PE-conjugated secondary antibody and analyzed by flow cytometry as described elsewhere (Krutzik et al., 2003. *Cytometry A* 55: 61-70).

Cell Lysis and Protein Extraction

Carcinoma cells cultured in monolayers were harvested by trypsinization, washed twice with DPBS and lysed for two hours on ice using immunoprecipitation lysis (IP) buffer (50 mM Tris-HCl, pH 7.5, 150 mM NaCl, 1 mM EDTA, 1 mM EGTA, 1% Triton X-100, 0.5% Nonidet P-40, 1 mM Na$_3$VO$_4$, 2 mM NaF) supplemented with fresh protease inhibitor cocktail (Cat #P8340, Sigma-Aldrich Biotechnology, St. Louis, MO) at 1:100 dilution. Insoluble materials were removed by centrifugation at 15,000×g for 10 minutes at 4° C., the supernatants were collected, and protein concentrations determined by BCA™ protein assay (Pierce Biotechnology Inc., Rockford, IL).

Immunoblot Analysis

Protein samples were boiled in 1× sample buffer (1% SDS in 31.25 mM Tris-HCl, pH 6.8 with 12.5% glycerol, 0.005% bromophenol blue and 2.5% betamercaptoethanol) for five minutes. SDS-polyacrylamide gels were loaded with 50 to 100 µg total protein per well as indicated, transferred to PVDF or nitrocellulose membranes by a Bio-Rad (Bio-Rad Laboratories, Inc., Hercules, CA) semi-dry protein transfer apparatus, blocked overnight with 5% skim milk in TBS-T buffer (20 mM Tris-HCl pH 7.4, 137 mM NaCl, 0.1% Tween-20), and incubated with the primary antibody diluted at 1:1000 for 1 hour in blocking buffer at room temperature. The blots were then washed three times for 5 minutes each with TBS-T and incubated for another one hour with horseradish peroxidase (HRP)-conjugated secondary antibody diluted at 1:3000 in blocking buffer. All antibodies to detect cell cycle regulators were purchased from Santa Cruz Biotechnology, Inc., (Santa Cruz, CA), except for phospho-PP2A-C (Tyr307) rabbit monoclonal antibody (Epitomics, Inc., Burlingame, CA). Final washes were performed three times with TBS-T before the blots were incubated in ECL Western Blotting Detection substrate (Amersham Biosciences, Piscataway, NJ). Chemiluminescent bands were documented and analyzed by exposing to Kodak XAR-5 X-ray film.

Co-Immunoprecipitation

An equal amount of lysate protein from each cell line was incubated with Ezview Red Protein A Affinity Gel (protein-A gel, Sigma-Aldrich) to minimize non-specific binding (pre-clear). The pre-cleared lysate was then mixed with 5 µg of capture antibody and the volume was adjusted to 1 ml with TBS. The mixture was incubated at 4° C. with gentle rotation for one hour, followed by addition of 25 µl of protein-A gel and incubation for an additional hour at 4° C. with gentle rotation. The protein-A-antibody-protein complex was then washed three times with cold immunoprecipitation lysis buffer and eluted from the protein-A gel with 1× sample buffer (as above). After brief centrifugation, the supernatants were incubated in boiling water for five minutes and analyzed by immunoblotting. For the 14-3-3β:Cdc25C interaction study, mouse anti-14-3-3β was used as co-IP capture antibody and rabbit anti-Cdc25C for immunoblot detection. Mouse anti-S100A8/A9 antibody 27E10 or anti-S100A9 and goat anti-PP2A-Aα antibody were used to co-immunoprecipitate S100A8/A9 and PP2A. All antibodies were purchased from Santa Cruz Biotechnology, Inc.

PP2A Inhibition by Okadaic Acid Treatment

KB, KB-EGFP and KB-S100A8/A9 cells were seeded at a density of 3×10$^5$ cells/well and cultured in complete medium overnight as described above. Cultured cells were incubated with fresh media containing 10 nM okadaic acid (Sigma-Aldrich, St. Louis, MO) or vehicle control (DMSO) for 24 hours. Cells were harvested by washing twice with cold DPBS and lysed directly in the well on ice with phosphatase lysis buffer (50 mM Tris-HCl, pH 7.5, 150 mM NaCl, 1% sodium deoxycholate, 1% SDS, 1% Triton X-100, 1 mM Na$_3$VO$_4$, 2 mM NaF and 10% protease inhibitor). Cell lysates were subjected to two freeze-thaw cycles at −80° C., centrifuged at 4° C. and supernatants collected for protein quantification by BCA and immunoblotting.

PP2A Phosphatase Activity Assay

Phosphatase activity was performed using the Immunoprecipitation Phosphatase Assay Kit (Cat #17-313, EMD Millipore, Billerica, MA). Synchronized cells were harvested, washed twice with DPBS, pelleted and resuspended in IP lysis buffer supplemented with fresh protease inhibitor cocktail as described above but without phosphatase inhibitors, Na$_3$VO$_4$ and NaF. Fresh cell lysates were used in each reaction. PP2A phosphatase activity was measured following the manufacturer's protocol. Briefly, 100 µg of total protein (concentration adjusted in IP lysis buffer) was mixed with 2 µg of mouse monoclonal capture antibody (PP2A, C subunit clone 1D6, EMD Millipore), isotype mouse IgG2b was used as control, and the volume was adjusted to 500 µl with pNPP Ser/Thr Assay Buffer (50 mM Tris-HCl, pH 7.0, 100 µM CaCl$_2$)), followed by one hour incubation at 4° C. with constant rocking. After incubation, 25 µl of protein A agarose beads were added to each reaction mixture and incubation continued with constant rocking for another one hour at 4° C. The beads were then washed three times with TBS, followed by one wash with Ser/Thr Assay Buffer and incubation in 750 µM threonine phosphopeptide (K-R-pT-I-R-R) solution diluted in Ser/Thr Assay Buffer for 10 minutes at 30° C. with constant shaking. Total inorganic phosphate (Pi) released was measured using Malachite Green phosphate detection solution (included in the kit).

Example 3

Cell Lines

Epithelial cells stably transfected to express calprotectin (KB-S100A8/A9, formerly known as KB-MRP8/14) or sham-control vector (KB-EGFP) were generated from KB cells as previously reported (Nisapakultorn et al., 2001. *Infect. Immun.* 69: 3692-3696). Briefly, KB cells were co-transfected with the mammalian expression vector, pIRES-EGFP (Clontech, Palo Alto, CA), containing S100A8 (MRP8) and S100A9 (MRP14) calprotectin subunit coding regions, and the selectable marker pSV2-neo (G418 sulfate-resistant marker). The resulting cell line, KB-S100A8/A9, expresses the calprotectin complex. The KB-EGFP sham-transfection control was generated by co-transfection of insert-less pIRES-EGFP and pSV2-neo. Both KB-S100A8/A9 and KB-EGFP were maintained in 700 µg/ml G418 sulfate (GENETICIN, Mediatech Inc., Manassas, VA) in MEM (CELLGRO, Mediatech, Inc., Manassas, VA), supplemented with 10% fetal bovine serum (FBS) and maintained at 5% CO2 at 37° C. Cells were maintained in MEM with 10% FBS without G418 (complete medium) for 2 days prior to all experiments.

TR146 cells are a buccal carcinoma cell line obtained from Dr. Reuben Lotan at the MD Anderson Cancer Center, Houston, TX Cells were cultured as above without G418. Some cells were stably transfected with shRNA to suppress expression and production of S100A8/A9 or with mock transfection control using standard methods.

Animal Model of Floor-of-the-Mouth Tumor Formation 6- to 8-week old female strain 01N70 [Cr:NIH(S)-nu/nu Nude] mice were housed and fed food and water ad libitum in microisolator cages in specific-pathogen-free conditions using a 12-hour light-dark cycle. Animals were anesthetized using 5% isofluorane in O$_2$ 2 L min$^{-1}$. KB (1×10$^5$) or TR146 (5×10$^4$) cells or transfected derivatives were suspended in 100 µl 1:1 Dulbecco's phosphate buffered saline (DPBS)/MATRIGEL (BD Biosciences, San Jose, CA) and injected orthotopically into the floor of the mouth. Animals were monitored until ambulatory and checked daily throughout the experiment. On day 17 post-injection, mice were euthanized with $CO_2$. Oral tissues including tumors were collected, rinsed in DPBS, preserved in 10% formalin solution paraffin-embedded and stained with hematoxylin and eosin (Histosery Inc, Germantown, MD) for histological analysis.

Figure 13:
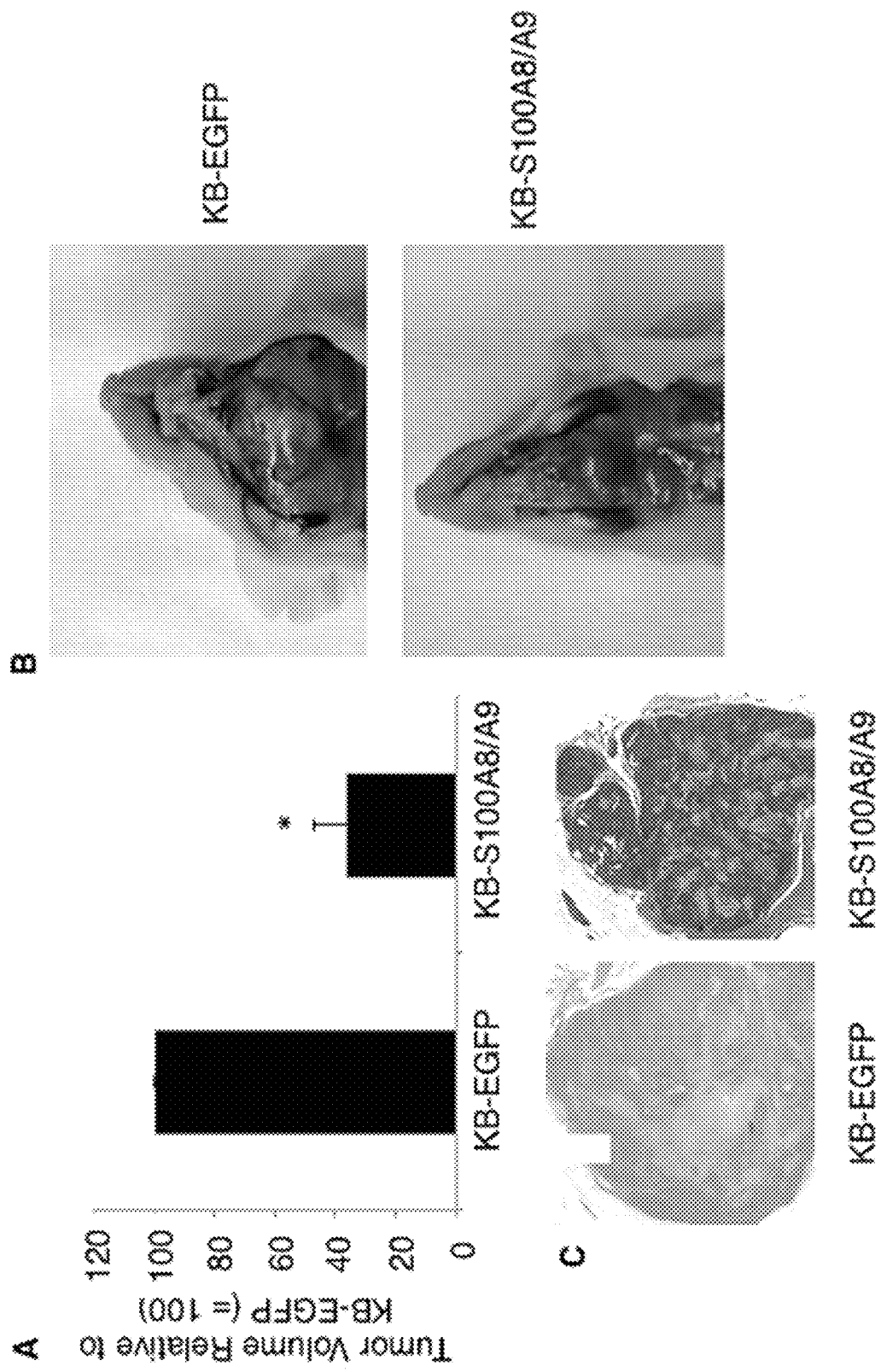
FIG. 13. Stable expression of S100A8/A9 reduces floor-of-the-mouth tumor growth. S100A8/A9 expressing KB carcinoma cells and sham transfected KB-cells expressing only EGFP were injected into the floor-of-the-mouth of separate groups of healthy mice as described in Example 3. (A) Orthotopic tumors formed by KB-S100A8/A9 cells on the floor-of-the-mouth from were 65% smaller by day 17 ($p<0.03$) than EGFP expressing KB cells. (B) Tumors formed on the floor-of-the-mouth from KB-S100A8/A9 cells are grossly smaller and less invasive into the surrounding tissues than KB-EGFP cell tumors. (C) KB-EGFP cell tumors are histologically (stained with hematoxylin and eosin) more de-differentiated and have larger areas of necrosis than similarly sized KB-S100A8/A9 cell tumors. Data shown are from three individual experiments, with three mice per group.
Figure 14:
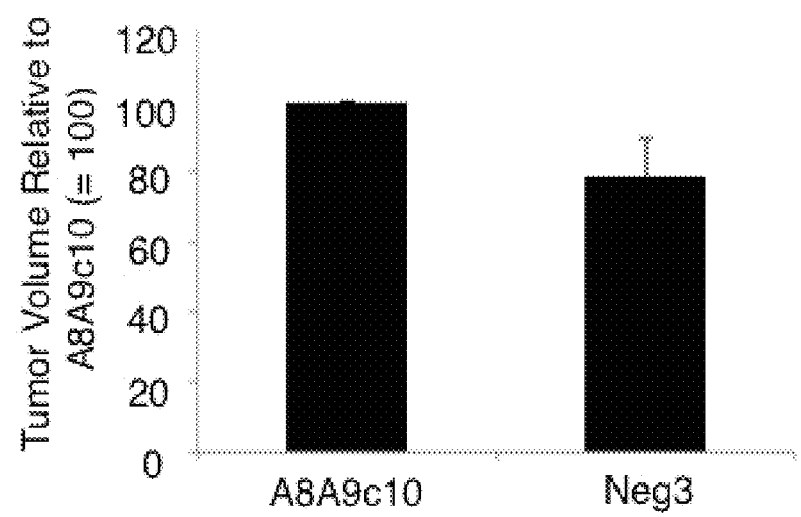
FIG. 14. Stable shRNA knockdown of S100A8/A9 correlates with larger floor-of-the-mouth tumor growth. TR146 buccal carcinoma cells were transfected with shRNA to stably knock down expression of endogenous S100A8 and S100A9. Knockdown resulted in approximately 70% less S100A8/A9 protein expression (A8A8c10 cells) than in sham-transfected cells (Neg3) (data not shown). TR146 cells with shRNA knockdown of S100A8/A9 (A8A8c10 cells) form orthotopic tumors that are 20% larger by day 17 ($p<0.2$) than sham transfected (Neg3) cells. Data shown are from two individual experiments, with three mice per group.

Results are shown in FIG. 13

Example 4

Templates were amplified from pGEM4Z.2bgUTR.150A as described in Example 1, with addition of 25% 2-thiouridine, the addition of 25% 5-methylcytidine, and mRNAs were synthesized using the mMESSAGE mMACHINE T7 Ultra Kit (Ambion, Life Technologies Corp., Grand Island, NY,) with ARCA capping. Cells were transfected using the TransIT-mRNA kit (Minis Bio LLC, Madison, WI). Saliva was collected from three donors immediately before transfection experiments, pooled, centrifuged at 12,000×g for five min to remove particulates, and the salivary supernatant was used for all experiments.

Saliva was diluted to show dose-response relationships, and incubated with the epithelial cell cultures for one minute, three minutes, or five minutes. In some experiments, saliva-treated cells were washed to reverse the treatment. Immediately after saliva treatments, with and without washes, cells were transfected with EGFP mRNA. 16 hours after mRNA transfection, cells were fixed with 4% paraformaldehyde for 10 minutes and nuclei were stained with DAPI. Fluorescent images were captured with an epifluorescence microscope. Results are shown in FIG. 15 and FIG. 16.

Example 5

Animal Model of Periodontitis and Efficacy of S100A8/A9 mRNA Treatments

Susceptibility to *P. gingivalis*-induced periodontitis is evaluated in wild-type C57BL/6 mice that are S100A8/A9−/−, S100A8/A9−/− mice with epithelial tissue-specific expression of human S100A8/A9, or S100A8/A9−/− mice receiving topically applied S100A8/A9 mRNA transfections to the gingival epithelium.

Oral Infection by *P. gingivalis*

*P. gingivalis* ATCC 53977 (A7A1-28) (Costalonga, et al., 2009, *J Periodontal Res* 44:537-542) induces the greater bone destruction than other *P. gingivalis* strains (Baker, et al., 2000, *Oral Microbiol Immunol* 15:27-32). To create oral infection, mice are pre-treated with antibiotics and fed $4 \times 10^9$ CFU *P. gingivalis* in 2% carboxymethylcellulose or control *L. murinus* by oral gavage, six episodes, four days apart as previously described (Costalonga, et al., 2009, *J Periodontal Res* 44:537-542). *L. murinus* does not cause periodontal bone loss or inflammation. *P. gingivalis* and *L. murinus* colonization is tested by sampling the oral cavity of mice before the first gavage and 50 days later.

Animals Used

C57BL/6J mice (The Jackson Laboratory, Bar Harbor, ME) are inoculated by oral gavage with *P. gingivalis* ATCC 53977. All mice are housed in a specific pathogen free (SPF) AAALAC-accredited facility. Based on previous power calculations, 21 mice receiving each treatment or control (sham) are sufficient to detect with 90% power differences of 10-15% in the extent of bone destruction around teeth (when a was set at 0.05) between *P. gingivalis* ATCC 53977-infected and sham-infected mice.

Measurement of Inflammation

Maxillae and mandibles are harvested at 0 and 50 days, dissected, and separated at the midline to obtain four specimens as described (Costalonga, et al., 2009, *J Periodontal Res* 44:537-542). Seven of the 14 right hemimandibles and hemimaxillas from each experimental group or treatment are fixed in 4% paraformaldehyde and decalcified in 10% EDTA at a pH of 8 for one week. Specimens are embedded in paraffin as described (Sato, et al., 1986, *Am J Pathol* 125:431-435) and stained with hematoxylin-eosin or frozen in OCT and processed for immunofluorescent identification of immune cells.

To characterize the cellularity of interproximal tissues, specimens of all three molars are sectioned meso-distally cutting 7 µm apico-coronally. The presence of inflammation and attachment loss is identified by the predominance of inflammatory nuclei and the apical migration of the junctional epithelium from the cementum-enamel junction, respectively.

Recovery of Bacteria from the Jaws

Immediately after harvesting, the other seven of 14 right hemimandibles and hemimaxillas are used to recover bacteria from the gingival epithelium by either stripping tissue from the bone or by treating the jaw with dispase to digest the epithelial layer from the connective tissues. Alternatively, the jaw is homogenized in pre-reduced culture media. A portion is plated on blood agar in an anaerobic chamber, and CFUs are enumerated. An aliquot also is used to estimate the levels of *P. gingivalis* and *L. murinus* using qPCR on the homogenate.

Determination of Alveolar Bone Loss

Left hemimandibles and hemimaxillas are defleshed gently using a scalpel. Jaws are boiled in distilled water for 10 minutes, placed in 1 N NaOH for three hours to remove the remaining keratinized gingiva, and finally stained with 1% methylene blue for one minute. Defleshed hemimandibles and hemimaxillas are mounted lingual-side-up on a pliable mold and photographed at 40× magnification under a stereomicroscope equipped with a digital camera as described (Costalonga, et al., 2009, *J Periodontal Res* 44:537-542). To minimize image distortion related to sample-objective angle, the lingual view of the hemimandibles and hemimaxillas are standardized so that the projected area between the distal edge of the buccal middle cusp and the distal edge of the lingual middle cusp is 10,000±500 pixels. Photographed jaws are measured from the cementum-enamel junction (CEJ) of each of the three molar teeth to the alveolar bone crest using a standardized grid in Adobe Photoshop (Adobe Systems, Inc., San Jose, CA). Alveolar bone level changes are measured indirectly as the number of pixels in the surface area of the visible root trunk as previously described (Costalonga, et al., 2009, *J Periodontal Res* 44:537-542).

In addition, some jaws are assessed using micro-computed tomography (CT).

Analyses

The average of the bone area measurements in the four independent groups (*P. gingivalis*-infected, *L. murinus*-infected control) in C57BL/6 mice and the S100A8/A9−/− mice are used as the dependent variable in an analysis of variance. The sensitivity of the measuring method allows detection of 10% changes in crestal bone levels with 90% power.

Similarly, the growth of bacteria generally and *P. gingivalis* and control *L. murinus* specifically in the presence and absence of S100A8/A9 is compared.

Inflammation is estimated semiquantitatively.

To evaluate the susceptibility to periodontitis in C57BL/6 wild-type and S100A8/A9−/− mice with epithelial-specific rescue of human S100A8/A9, *P. gingivalis* or control *L. murinus* are used to infect wild-type C57BL/6 (murine S100A8/A9+/+) mice, S100A8/A9−/− mice, and S100A8/A9−/− mice rescued by knock-in with human epithelial-specific S100A8 and S100A9. The null mutation for S100A8/A9 in mice of the C57BL/6 background are rescued using a system to introduce multiple genes into the mouse using transposon integratable multigene vectors (Moriarity et al., 2013, *Nucleic Acids Res* 41:e92). Using this system, one can target the ROSA26 locus (Soriano, P. 1999, *Nature Genetics* 21:70-71) with the multigene vector containing the coding regions for S100A8 and S100A9 to knock-in with a K14 promoter. Hence, the knock-in is only expressed in epithelial cells. Expression of human S100A9 can permit translation of mouse S100A8 in the S100A8/A9−/− mice because mouse S100A8 does not complex with human S100A9 to form hybrid heterodimers (Propper et al., 1999, *J Biol Chem* 274:183-188).

The three strains of mice are compared for expression of periodontitis as described above using *P. gingivalis* as pathogen and *L. murinus* as commensal, non-pathogenic control.

Periodontitis is expressed similarly in wild-type C57BL/6 (murine S100A8/A9+/+) and human epithelial-specific knock-in (S100A8/A9−/− background) strains. The S100A8/A9−/− mice show the greatest amount of alveolar bone loss.

This experiment shows that the coding regions for S100A8 and S100A9 are innate immune factors in the resistance to periodontitis. Comparing the soft tissue histopathology of the three strains before and after establishing periodontitis confirms the localization of human and murine S100A8/A9 in the gingival epithelium and the loss of epithelial integrity after infection in the S100A8/A9−/− mouse.

Knock-in of Human Epithelial-Specific S100A8/A9

Epithelia-specific S100A8/A9 is knocked into S100A8/A9−/− ES cells using the integratable multigene vector (Moriarity et al., 2013, *Nucleic Acids Res* 41:e92) targeting the ROSA26 locus. A lox-stop-lox cassette is placed between a K14 promoter and the multigene vector containing human S100A8 and S100A9 coding regions. (Human S100A8/A9 forms as a complex spontaneously within epithelial cells (Champaiboon et al., 2009, *J Biol Chem* 284:7078-7090)). Mice homozygous for Keratin14-CRE and the multigene (S100A8 and S100A9)$^{cre}$ conditional allele are crossed to generate experimental mice. Successfully crossed mice express S100A8/A9 in epithelial tissues. The mouse described herein as S100A8/A9−/− is actually S100A9−/−, expressing S100A8 mRNA but not S100A8 protein (Hobbs et al., 2003, *Mol Cell Biol* 23:2564-2576; Manitz et al., 2003, *Mol Cell Biol* 23:1034-1043). The murine S100A8/A9 remains intact so that S100A8/A9 overexpression is solely from the floxed-in human proteins.

Assessment of Periodontitis

Using the methods and approach described above, inflammation is estimated and *P. gingivalis* infection of the epithelium and alveolar bone levels in *P. gingivalis*-infected, wild-type, S100A8/A9−/− and human S100A8/A9 knock-in (S100A8/A9−/− background) is measured at the start of the experiment and at 50 days after initial inoculation. Data are compared to *L. murinus*-infected (control) mice of each background to determine the role of S100A8/A9 in resistance to *P. gingivalis* infection.

Analyses

The average of the bone area measurements is used as the dependent variable in an analysis of variance in the six independent groups (*P. gingivalis*-infected, *L. murinus*-infected control) in C57BL/6 mice, S100A8/A9−/− mice, and human S100A8/A9 rescued mice in the S100A8/A9−/− background. The sensitivity of the measuring method allows detection of 10% changes in crestal bone levels with 90% power. Similarly, the growth of bacteria generally in the epithelium and *P. gingivalis* and control *L. murinus* specifically in the presence and absence of S100A8/A9 are compared.

Inflammation is estimated semiquantitatively.

To evaluate the susceptibility to periodontitis in C57BL/6 S100A8/A9−/− mice with and without S100A8/A9 mRNAs applied topically to the gingiva, *P. gingivalis* or control *L. murinus* are used to infect wild-type (murine S100A8/A9+/+) mice, S100A8/A9−/− mice, and S100A8/A9−/− mice rescued by topical application of packaged human S100A8/A9 mRNA. Epithelial cells can be transfected with mRNAs specific for S100A8 and S100A9 to express both proteins and form antimicrobial S100A8/A9 complex (Zou et al., 2013, *Infect Immun* 81:3975-3983). The transfection system is essentially topical. Packaged mRNAs are added directly to the epithelial surface, the mRNA is taken up into the epithelial cells, new S100A8 and S100A9 proteins are co-expressed in the same cell and resistance to invading bacterial pathogens increases.

For in vivo experiments, saliva is washed from the mouse oral epithelium to reduce the salivary barrier to uptake of the packaged mRNAs. The epithelium is air dried prior to applying the packaged mRNAs directly to the tooth-gingival interface using a high intensity atomizer essentially as described for use in lungs (Kormann et al., 2011, *Nature Biotechnology* 29:154-157; Mays et al., 2013, *J Clin Invest* 123:1216-1228). The atomizer is fitted with a narrow aperture needle to enable direction of the mRNA to the intended interface.

S100A8/A9 mRNA is applied to the gingiva one day before each application of *P. gingivalis* to minimize interference with either protocol. Mice in the three conditions are compared for expression of periodontitis as described above using *P. gingivalis* as pathogen and *L. murinus* as commensal, non-pathogenic control. Periodontitis is evident similarly in wild-type (murine S100A8/A9+/+) and S100A8/A9−/− mice rescued by topical application of packaged human S100A8/A9 mRNA. The S100A8/A9−/− mice show the greatest amount of alveolar bone loss.

This experiment confirms that S100A8 and S100A9 are innate immune factors in gingival epithelial resistance to periodontitis. Comparing the soft tissue histopathology of mice in the three conditions before and after establishing periodontitis confirms the localization of human and murine S100A8/A9 in the gingival epithelium and the loss of epithelial integrity after infection in the S100A8/A9−/− mouse.

Analyses

The average of the bone area measurements is used as the dependent variable in an analysis of variance in the six independent groups (*P. gingivalis*-infected, *L. murinus*-infected control) in wild-type (murine S100A8/A9+/+) mice, S100A8/A9−/− mice, and S100A8/A9−/− mice rescued by topical application of packaged human S100A8/A9 mRNA. Analyses are as described above.

EXEMPLARY EMBODIMENTS

Embodiment 1

A method comprising:
introducing into an epithelial cell an mRNA encoding a polypeptide involved in suppressing cell proliferation; and
permitting the cell to express the polypeptide in an amount effective to decrease the likelihood that the cell proliferates in an anchorage-independent environment.

Embodiment 2

The method of Embodiment 1 wherein the polypeptide comprises calprotectin, S100A8, or S100A9.

Embodiment 3

A method comprising:
introducing into a cell an mRNA encoding a polypeptide involved in innate immunity; and
permitting the cell to express the polypeptide in an amount effective to decrease the likelihood that the cell is infected by a pathogen.

Embodiment 4

The method of Embodiment 3 wherein the polypeptide comprises cathelicin antimicrobial protein (CAMP), calprotectin, S100A8, S100A9, a β-defensin, S100A7, secretory leukocyte inhibitor, lipocalin 2, or lysozyme.

Embodiment 5

The method of any preceding Embodiment wherein the mRNA comprises a stabilizing moiety.

Embodiment 6

The method of Embodiment 5 wherein the stabilizing moiety comprises a 5' cap.

Embodiment 7

The method of Embodiment 5 wherein the stabilizing moiety comprises a 3' extension.

Embodiment 8

The method of any preceding Embodiment wherein the cell is a mucosal epithelial cell.

Embodiment 9

The method of any one of Embodiments 3-8 further comprising permitting the cell to be exposed to the pathogen.

Embodiment 10

The method of any one of Embodiments 3-9 wherein the pathogen comprises a bacterium.

Embodiment 11

The method of Embodiment 10 wherein the bacterium comprises *Capnocytophaga sputigena, Escherichia coli*, a *Staphylococcus* spp., a *Streptococcus* spp., *Listeria monocytogenes, Salmonella typhimurium, Borrelia burgdorferi, Porphyromonas gingivalis, Tannerella forsythia, Treponema denticola, Pseudomonas aeruginosa*, a *Chlamydia* spp., a *Neisseria* spp., a *Gardnerella* spp., or a *Trichomonas* spp.

Embodiment 12

The method of any one of Embodiments 3-9 wherein the pathogen comprises a fungus.

Embodiment 13

The method of Embodiment 12 wherein the fungus comprises fungi *Candida albicans, Acinetobacter baumannii*, or an *Aspergillus* spp.

Embodiment 14

The method of any one of Embodiments 3-13 wherein the cell is a cell of a subject having or at risk of having a condition caused by infection by the pathogen.

Embodiment 15

The method of Embodiment 14 wherein the condition comprises a carcinoma.

Embodiment 16

The method of any preceding Embodiment further comprising washing the cell to remove mucosal fluid from the cell prior to introducing the mRNA into the cell.

Embodiment 17

The method of Embodiment 16 wherein the mucosal fluid comprises saliva.

Embodiment 18

A composition comprising:
an mRNA that encodes a polypeptide that suppresses cell proliferation in an epithelial cell; and
an in vivo delivery vehicle.

Embodiment 19

The composition of Embodiment 18 wherein the polypeptide comprises calprotectin, S100A8, or S100A9.

Embodiment 20

The composition of Embodiment 18 or Embodiment 19 wherein the polypeptide suppresses cell proliferation of the epithelial cell when the epithelial cell is grown in an anchorage-independent environment.

Embodiment 21

A composition comprising:
an mRNA that encodes a polypeptide involved in innate immunity; and
an in vivo delivery vehicle.

Embodiment 22

The composition of Embodiment 21 wherein the polypeptide comprises cathelicin antimicrobial protein (CAMP), calprotectin, S100A8, S100A9, a β-defensin, S100A7, secretory leukocyte inhibitor, lipocalin 2, or lysozyme.

Embodiment 23

The composition of any one of Embodiments 18-22 wherein the mRNA comprises a stabilizing moiety.

Embodiment 24

The composition of Embodiment 23 wherein the stabilizing moiety comprises a 5' cap.

Embodiment 25

The composition of Embodiment 23 wherein the stabilizing moiety comprises a 3' extension.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for increasing resistance to a pathogen in a subject comprising:
topically applying to a mucosal squamous epithelial cell of the subject a composition comprising (i) at least one in vitro transcribed isolated mRNA that comprises a synthetic 5' cap and that encodes at least two polypeptides involved in innate immunity, wherein the polypeptides comprise cathelicidin antimicrobial protein (CAMP) and calprotectin, and (ii) a pharmaceutically acceptable in vivo delivery vehicle formulated for topical application to the mucosal squamous epithelial cell, whereby the topical application provides transfection in vim of the isolated mRNA to express the polypeptides in an amount effective to increase resistance to a pathogen in the mucosal squamous epithelial cell.

2. The method of claim 1, wherein the composition is topically applied to mucosal squamous epithelial cells of an oral cavity of the subject.

3. The method of claim 1, wherein the mucosal squamous epithelial cell is an oral mucosal squamous epithelial cell.

4. The method of claim 1, wherein the at least one in vitro transcribed isolated mRNA further comprises mRNA selected from S100A8, S100A9 and calprotectin with an internal ribosomal entry site (IRES) inserted between S100A8 and S100A9 (A8-IRES-A9) mRNAs.

5. The method of claim 1, wherein the at least two polypeptides involved in innate immunity further comprise polypeptides selected from S100A8, S100A9, a β-defensin, S100A7, secretory leukocyte inhibitor, lipocalin 2, and lysozyme.

6. The method of claim 1, wherein the 5' cap is anti-reverse cap analogue (ARCA), capping enzyme (CE) cap 0, or CE cap 1.

7. The method of claim 1, wherein the at least one in vitro transcribed isolated mRNA additionally comprises a 3' extension.

8. The method of claim 1, wherein the at least one in vitro transcribed isolated mRNA comprises methylcytidine and 2-thiouridine.

9. The method of claim 4, wherein the at least one in vitro transcribed isolated mRNA further encodes polypeptides involved in innate immunity selected S100A8 and S100A9.

10. The method of claim 1, wherein the at least one in vitro transcribed isolated mRNA encodes lipocalin 2.

11. The method of claim 1, wherein the at least one in vitro transcribed isolated mRNA that encodes calprotectin is selected from the mRNAs of calprotectin or A8-IRES-A9 mRNAs.

12. The method of claim 1, wherein the pathogen is a bacterium or a fungus.

13. The method of claim 12, wherein the bacterium is *Capnocytophaga sputigena*, *Escherichia coli*, a *Staphylococcus* spp., a *Streptococcus* spp., *Listeria monocytogenes*, *Salmonella typhimurium*, *Borrelia burgdorferi*, *Porphyromonas gingivallis*, *Tannerella forsythia*, *Treponema denticola*, *Pseudomonas aeruginosa*, a *Chlamydia* spp., a *Neisseria* spp., a *Gardnerella* spp., or a *Trichomonas* spp.

14. The method of claim 12, wherein the fungus is selected from the group consisting of *Candida albicans*, *Acinetobacter baumannii*, and an *Aspergillus* spp.

15. The method of claim 1, further comprising the step of washing the mucosal squamous epithelial cell to remove mucosal fluid prior to topically applying the composition.

16. A method for treating inflammatory or hyperproliferative oral lesions in a subject comprising:
topically applying to an oral mucosal squamous epithelial cell of the inflamed or the hyperproliferative oral lesion a composition comprising: (i) at least one in vitro transcribed isolated mRNA that comprises a synthetic 5' cap and that encodes at least one polypeptide involved in suppressing cell proliferation wherein the at least one polypeptide comprises a polypeptide selected from the group consisting of calprotectin, S100A8, and S100A9, and (ii) a pharmaceutically acceptable in vivo delivery vehicle formulated for topical application, whereby the in vitro transcribed isolated mRNA transfected in vivo expresses the polypeptide in the cell in an amount effective to treat the inflammatory or the hyperproliferative oral lesion and the composition prevents carcinogenesis of the inflammatory or the hyperproliferative oral lesion or treats the inflammatory or the hyperproliferative oral lesion that is cancerous.

17. The method of claim 16, wherein the 5' cap is ARCA, CE cap 0, or CE cap 1.

18. The method of claim 16, wherein the at least one in vitro transcribed isolated mRNA additionally comprises a 3' extension.

19. The method of claim 16, wherein the at least one in vitro transcribed isolated mRNA comprises methylcytidine and 2-thiouridine.

20. The method of claim 16, wherein the at least one in vitro transcribed isolated mRNA is selected from the mRNAs of CAMP, calprotectin, S100A8, S100A9, and A8-1 RES-A9.

21. The method of claim 16, further comprising the step of washing the mucosal squamous epithelial cell to remove mucosal fluid prior to topically applying the mRNA composition.

22. The method of claim 16, wherein the carcinogenesis of the lesion or cancerous lesion is squamous cell carcinoma.

23. The method of claim 16, wherein the composition additionally comprises IL-1α, IL-1α with keratinocyte growth factor, IL-6, IL-8, IL-8 with CXCL8, IL-22, TNFα, CXCL1, CXCL2, CXCL3, or CCL20.

24. A method for treating a pathogen infection in a subject comprising:
   introducing into a mucosal squamous epithelial cell of the subject a composition comprising (i) at least one in vitro transcribed isolated mRNA that comprises a synthetic 5' cap and that encodes at least two polypeptides, wherein the polypeptides comprise CAMP and calprotectin, and (ii) a pharmaceutically acceptable in vivo delivery vehicle, wherein introducing comprises topically applying the composition to the mucosal squamous epithelial cell,
   whereby the introduction of the composition provides transfection in vivo of the isolated mRNA to express the polypeptides in the cell in an amount effective to treat the pathogen infection in the transfected mucosal squamous epithelial cell.

25. The method of claim 24, wherein the at least two polypeptides further comprise a polypeptide selected from the group consisting of S100A8, S100A9, B-defensin, S100A7, secretory leukocyte inhibitor, lipocalin 2, and lysozyme.

* * * * *

UNITED STATES PATENT AND TRADEMARK OFFICE
CERTIFICATE OF CORRECTION

PATENT NO. : 11,912,744 B2
APPLICATION NO. : 16/842489
DATED : February 27, 2024
INVENTOR(S) : Mark C. Herzberg et al.

It is certified that error appears in the above-identified patent and that said Letters Patent is hereby corrected as shown below:

In the Specification

Column 16, Line 67, "566" should be --56δ--.

Column 17, Line 10, "PP2A-Aa/β" should be --PP2A-Aα/β--.

Column 17, Line 12, "Aa/β, B566 and Ca/β" should be --Aα/β, B56δ and Cα/β--.

Column 17, Line 13, "Ca/β" should be --Cα/β--.

Column 17, Line 28, "PP2A-Aa/β" should be --PP2A-Aα/β--.

Column 19, Line 44, "Ca/β" should be --Cα/β--.

Column 20, Line 53, "PP2Adependent" should be --PP2A-dependent--.

Column 26, Line 12, "104035" should be --10403S--.

Column 26, Line 34, "XhoI" should be --XhoI--.

Column 27, Line 36, "Minis" should be --Mirus--.

Column 33, Lines 4-5, "Histosery" should be --Histoserv--.

Column 33, Line 16, "Minis" should be --Mirus--.

Column 33, Line 66, "a was" should be --α was--.

Signed and Sealed this
Fourteenth Day of May, 2024

Katherine Kelly Vidal
*Director of the United States Patent and Trademark Office*

CERTIFICATE OF CORRECTION (continued)
U.S. Pat. No. 11,912,744 B2

In the Claims

Column 45, Claim 1, Line 43, "vim" should be --vivo--.

Column 48, Claim 25, Line 23, "B-defensin" should be --β-defensin--.

SEQUENCE LISTING

```
<160> NUMBER OF SEQ ID NOS: 20

<210> SEQ ID NO 1

<400> SEQUENCE: 1

000

<210> SEQ ID NO 2
<211> LENGTH: 29
<212> TYPE: DNA
<213> ORGANISM: artificial
<220> FEATURE:
<223> OTHER INFORMATION: synthetic oligonucleotide primer

<400> SEQUENCE: 2
cctaagcttg ccaccatggt gagcaaggg                                29

<210> SEQ ID NO 3
<211> LENGTH: 39
<212> TYPE: DNA
<213> ORGANISM: artificial
<220> FEATURE:
<223> OTHER INFORMATION: synthetic oligonucleotide primer

<400> SEQUENCE: 3
atttgcggcc gcttacttgt acagctcgtc catgccgag                     39

<210> SEQ ID NO 4
<211> LENGTH: 37
<212> TYPE: DNA
<213> ORGANISM: artificial
<220> FEATURE:
<223> OTHER INFORMATION: synthetic oligonucleotide primer

<400> SEQUENCE: 4
```
cctaagcttg ccaccatgaa gacccaaagg gatggcc                                37

<210> SEQ ID NO 5
<211> LENGTH: 41
<212> TYPE: DNA
<213> ORGANISM: artificial
<220> FEATURE:
<223> OTHER INFORMATION: synthetic oligonucleotide primer

<400> SEQUENCE: 5
atttgcggcc gcctaggact ctgtcctggg tacaagattc c                           41

<210> SEQ ID NO 6
<211> LENGTH: 39
<212> TYPE: DNA
<213> ORGANISM: artificial
<220> FEATURE:
<223> OTHER INFORMATION: synthetic oligonucleotide primer

<400> SEQUENCE: 6
cctaagcttg ccaccatgtt gaccgagctg gagaaagcc                              39

<210> SEQ ID NO 7
<211> LENGTH: 38
<212> TYPE: DNA
<213> ORGANISM: artificial
<220> FEATURE:
<223> OTHER INFORMATION: synthetic oligonucleotide primer

<400> SEQUENCE: 7
atttgcggcc gcctactctt tgtggctttc ttcatggc                               38

<210> SEQ ID NO 8
<211> LENGTH: 39
<212> TYPE: DNA
<213> ORGANISM: artificial
<220> FEATURE:
<223> OTHER INFORMATION: synthetic oligonucleotide primer

<400> SEQUENCE: 8
cctaagcttg ccaccatgac ttgcaaaatg tcgcagctg                              39

<210> SEQ ID NO 9
<211> LENGTH: 30
<212> TYPE: DNA
<213> ORGANISM: artificial
<220> FEATURE:
<223> OTHER INFORMATION: synthetic oligonucleotide primer

<400> SEQUENCE: 9
atttgcggcc gcttaggggg tgccctcccc                                        30

<210> SEQ ID NO 10
<211> LENGTH: 39
<212> TYPE: DNA
<213> ORGANISM: artificial
<220> FEATURE:
<223> OTHER INFORMATION: synthetic oligonucleotide primer

<400> SEQUENCE: 10
cctaagcttg ccaccatgtt gaccgagctg gagaaagcc                              39

<210> SEQ ID NO 11
<211> LENGTH: 30
<212> TYPE: DNA

```
<213> ORGANISM: artificial
<220> FEATURE:
<223> OTHER INFORMATION: synthetic oligonucleotide primer

<400> SEQUENCE: 11
atttgcggcc gcttaggggg tgccctcccc                                   30

<210> SEQ ID NO 12

<400> SEQUENCE: 12

000

<210> SEQ ID NO 13
<211> LENGTH: 38
<212> TYPE: DNA
<213> ORGANISM: artificial
<220> FEATURE:
<223> OTHER INFORMATION: synthetic oligonucleotide primer

<400> SEQUENCE: 13
ctagctagcg ccaccatgtt gaccgagctg gagaaagc                          38

<210> SEQ ID NO 14
<211> LENGTH: 35
<212> TYPE: DNA
<213> ORGANISM: artificial
<220> FEATURE:
<223> OTHER INFORMATION: synthetic oligonucleotide primer

<400> SEQUENCE: 14
ccgctcgagc tactctttgt ggctttcttc atggc                             35

<210> SEQ ID NO 15
<211> LENGTH: 38
<212> TYPE: DNA
<213> ORGANISM: artificial
<220> FEATURE:
<223> OTHER INFORMATION: synthetic oligonucleotide primer

<400> SEQUENCE: 15
gctctagagc caccatgact tgcaaaatgt cgcagctg                          38

<210> SEQ ID NO 16
<211> LENGTH: 30
<212> TYPE: DNA
<213> ORGANISM: artificial
<220> FEATURE:
<223> OTHER INFORMATION: synthetic oligonucleotide primer

<400> SEQUENCE: 16
atttgcggcc gcttaggggg tgccctcccc                                   30

<210> SEQ ID NO 17
<211> LENGTH: 22
<212> TYPE: DNA
<213> ORGANISM: artificial
<220> FEATURE:
<223> OTHER INFORMATION: synthetic oligonucleotide primer

<400> SEQUENCE: 17
aaacgtctag gccccccgaa cc                                           22

<210> SEQ ID NO 18
<211> LENGTH: 34
<212> TYPE: DNA
```

```
<213> ORGANISM: artificial
<220> FEATURE:
<223> OTHER INFORMATION: synthetic oligonucleotide primer

<400> SEQUENCE: 18
tttaacctcg actaaacaca tgtaaagcat gtgc                          34

<210> SEQ ID NO 19
<211> LENGTH: 27
<212> TYPE: DNA
<213> ORGANISM: artificial
<220> FEATURE:
<223> OTHER INFORMATION: synthetic oligonucleotide primer

<400> SEQUENCE: 19
accatgactt gcaaaatgtc gcagctg                                  27

<210> SEQ ID NO 20
<211> LENGTH: 31
<212> TYPE: DNA
<213> ORGANISM: artificial
<220> FEATURE:
<223> OTHER INFORMATION: synthetic oligonucleotide primer

<400> SEQUENCE: 20
attatcatcg tgttttcaa aggaaaacca c                              31
```